United States Patent [19]
Danishefsky et al.

[11] Patent Number: 5,543,505
[45] Date of Patent: Aug. 6, 1996

[54] SYNTHETIC COMPOUNDS WHICH BIND TO H. PYLORI, AND USES THEREOF

[75] Inventors: Samuel J. Danishefsky, New Haven, Conn.; John T. Randolph, New York, N.Y.

[73] Assignee: Sloan-Kettering Institute for Cancer Research, New York, N.Y.

[21] Appl. No.: 213,053

[22] Filed: Mar. 15, 1993

[51] Int. Cl.$^6$ .................. C07H 15/00; C07H 15/06; C07H 17/00; C07K 1/00
[52] U.S. Cl. .............. 536/17.2; 536/17.5; 536/17.9; 536/18.2; 536/123.1; 530/300; 530/322; 530/350; 530/363
[58] Field of Search ................ 536/17.2, 17.5, 536/17.9, 18.2, 123.1; 530/300, 322, 350, 363

[56] References Cited

FOREIGN PATENT DOCUMENTS

93/05803  4/1993  WIPO .

OTHER PUBLICATIONS

Alper, Joseph, "New Bind for Ulcer Bacterium" *Science*, vol. 262, 1817 (17 Dec. 1993); U.S.A. (Exhibit B).
Altman, Lawrence K., "Stomach Microbe Offers Clues for Cancer as Well as Ulcers," *The New York Times*, C3 (Feb. 22, 1994); U.S.A. (Exhibit C).

(List continued on next page.)

*Primary Examiner*—Douglas W. Robinson
*Assistant Examiner*—Everett White
*Attorney, Agent, or Firm*—John P. White

[57] ABSTRACT

The present invention provides a compound having the structure:

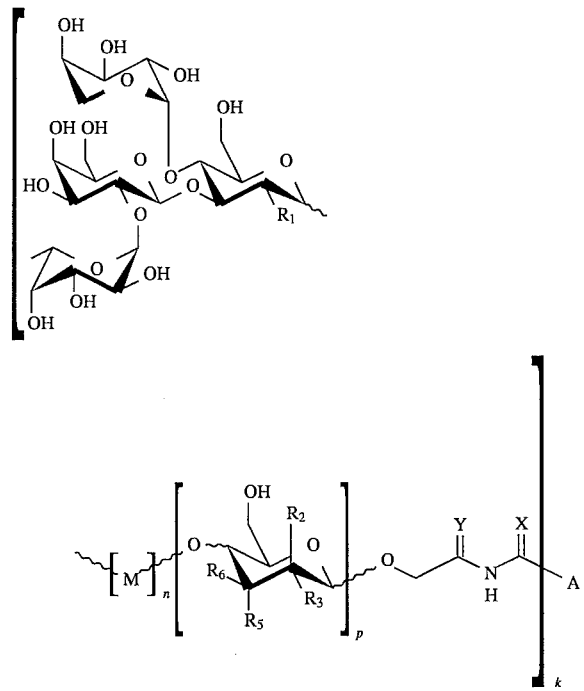

wherein A is selected from the group consisting of (i) an amino acid bearing an ω-amino group or an ω—(C=O)— group, (ii) an amino acid residue of a peptide, which residue bears an ω-amino group or an ω-(C=O)— group, and (iii) an amino acid residue of a protein, which residue bears an ω-amino group or an ω-(C=O)— group; wherein $R_1$ is H, OH, $NH_2$ or $NHR_4$, where $R_4$ is $SO_2Ph$, a linear or branched chain alkyl or acyl group, or an aryl group; wherein M is a saccharide wherein n is an integer from 0 to 18, and where n is greater than 1, each M is independently the same or different; wherein p is either 0 or 1; wherein $R_2$, $R_3$, $R_5$ and $R_6$ are independently the same or different and are H or OH, with the proviso that $R_2$ and $R_3$ are not both OH, and $R_5$ and $R_6$ are not both OH; wherein X and Y are independently the same or different and are $H_2$ or O; and wherein k is an integer greater than or equal to 1, with the proviso that when A is an amino acid bearing an ω-amino group or an ω-(C=O)— group, k is equal to 1.

8 Claims, 8 Drawing Sheets

OTHER PUBLICATIONS

Bernstein, Michael A., and Hall, Laurance D., "A general synthesis of model glycoproteins: coupling of alkenyl glycosides to proteins, using reductive ozonolysis followed by reductive amination with sodium cyanoborohydride," *Carbohydrate Research,* 78, C1–C3 (1980); The Netherlands (Exhibit D).

Boren, Thomas, Falk, Per, Roth, Kevin A., Larson, Goran, Normark, Staffan, "Attachment of *Helicobacter pylori* to Human Gastric Epithelium Mediated by Blood Group Antigens" Science, vol. 262, 1892–1895 (17 Dec. 1993); U.S.A. (Exhibit E).

Falk, Per, Boren, Thomas and Normark, Staffan, "Strategies for Characterization of Microbial Host Receptors," Methods in Enzymology, vol. 236, 0000 (1994); U.S.A. (Exhibit G).

Falk, Per, Roth, Kevin A. Boren, Thomas, Westblom, T. Ulf, Gordon, Jeffrey T. and Normark, Staffan, "An in vitro adherence assay reveals that *Helicobacter pylori* exhibits cell lineage–specific tropism in the human gastric epithelium," Proc. Natl. Acad. Sci. U.S.A., vol. 90, 2035–2039 (Mar. 1993); U.S.A. (Exhibit H).

Gray, G.R., "Antibodies to Carbohydrates: Preparation of Antigens by Coupling Carbohydrates to Proteins by Reductive Amination with Cyanoborohydride," *Methods in Enzymology,* vol. 50, 155–160 (1978); U.S.A. (Exhibit I).

Mahajan, R., Dixit, S., Khare, N. K. and Khare, A., "Synthesis of Neoglycoproteins as artificial Antigens," *Carbohydrate Chemistry,* vol. 13(1), 63–73 (1994); U.S.A. (Exhibit J).

Chemical Abstracts, vol. 109, No. 15, issued 1988, Ogawa eet al., "Glyco–sphingolipids Bearing a Lewis b Type Antigenic Determinant and a Process for their Preparation", p. 752, column 2, abstract No. 129595w, Jpn. Kokai Tokkyo Koho JP 63 51, 396.

17: R=CH₂CH=CH

SYNTHETIC COMPOUNDS WHICH BIND TO H. PYLORI, AND USES THEREOF

This invention was made with government support under grants GM-15240-02, CA-28824, and AI-16943 from the National Institutes of Health. Accordingly, the U.S. Government has certain rights in the invention.

BACKGROUND OF THE INVENTION

Throughout this application, citations for various publications are provided within parentheses in the text. The disclosures of these publications are hereby incorporated in their entirety by reference into this application in order to more fully describe the state of the art to which this invention pertains.

The function of carbohydrates as structural materials and as energy storage units in biological systems is well recognized. By contrast, the role of carbohydrates as signaling molecules in the context of biological processes has only recently been appreciated. (M. L. Phillips, E. Nudelman, F. C. A. Gaeta, M. Perez, A. K. Singhal, S. Hakomori, J. C. Paulson, Science 1990, 250, 1130; M. J. Polley, M. L. Phillips, E. Wagner, E. Nudelman, A. K. Singhal, S. Hakomori, J. C. Paulson, Proc. Natl. Acad. Sci. USA 1991, 88, 6224: T. Taki, Y. Hirabayashi, H. Ishikawa, S. Kon, Y. Tanaka, M. Matsumoto, J. Biol. Chem. 1986, 261, 3075; Y. Hirabayashi, A. Hyogo, T. Nakao, K. Tsuchiya, Y. Suzuki, M. Matsumoto, K. Kon, S. Ando, ibid., 1990, 265, 8144; O. Hindsgaul, T. Norberg, J. Le Pendu, R. U. Lemieux, Carbohydr. Res. 1982, 109, 109; U. Spohr, R. U. Lemieux, ibid., 1988, 174, 211).

The elucidation of the scope of carbohydrate involvement in mediating cellular interaction is an important area of inquiry in contemporary biomedical research. The carbohydrate molecules, carrying detailed structural information, tend to exist as glycoconjugates (cf. glycoproteins and glycolipids) rather than as free entities. Given the complexities often associated with isolating the conjugates in homogeneous form, and the difficulties in retrieving intact carbohydrates from these naturally occurring conjugates, the opportunities for synthesis are apparent. (For recent reviews of glycosylation see: Paulsen, H., Agnew. Chemie Int. Ed. Engl. 1982, 21, 155; Schmidt, R. R., Angew. Chemie Int. Ed. Engl. 1986, 25, 212; Schmidt, R. R., Comprehensive Organic Synthesis, Vol. 6, Chapter 1 (2) Pergamom Press, Oxford, 1991; Schmidt, R. R., Carbohydrates, Synthetic Methods and Applications in Medicinal Chemistry, Part I, Chapter 4, VCH Publishers, Weinheim, New York, 1992. For pioneering work on the use of glycals as glycosyl donors in glycoside synthesis see Lemieux, R. U., Can. J. Chem. 1964, 42, 1417; Lemieux, R. U., Faser-Reid, B. Can. J. Chem. 1965, 42, 1460; Lemieux, R. U., Morgan, A. R., Can. J. Chem. 1965, 43, 2190; Thiem, J., Karl, H., Schwentner, J., Synthesis 1978, 696; Thiem. J. Ossowski, P., Carbohydr. Chem. 1984, 3, 287; Thiem, J., Prahst, A., Wendt, T. Liebigs Am. Chem. 1986, 1044; Thiem, J. in Trends in Synthetic Carbohydrate Chemistry, Horton, D., Hawkins, L. D., McGarvvey, G. L. (Eds.), ACS Symposium Series #386, American Chemical Society, Washington, D.C., 1989, Chapter 8.)

The carbohydrate domains of the blood group substances, contained in both glycoproteins and glycolipids, are distributed in erythrocytes, epithelial cells and in various secretions. The early focus on these systems centered on their central role in determining blood group specificities. (R. R. Race, R. Sanger, Blood Groups in Man, 6th ed., Blackwell, Oxford, 1975) However, it is recognized that such determinants are broadly implicated in cell adhesion and binding phenomena. (For example, see M. L. Phillips, E. Nudelman, F. C. A. Gaeta, M. Perez, A. K. Singhal, S. Hakomori, J. C. Paulson, Science 1990, 250, 1130.) Moreover, ensembles related to the blood group substances in conjugated form are encountered as markers for the onset of various tumors. (K. O. Lloyd, Am. J. Clinical Path. 1987, 87, 129; K. O. Lloyd Cancer Biol. 1991, 2, 421) Carbohydrate-based tumor antigenic factors might find applications at the diagnostic level, as resources in drug delivery, or, ideally, in immunotherapy. (T. Toyokuni, B. Dean, S. Cai, D. Boivin, S. Hakomori A. K. Singhal, J. Am. Chem Soc. 1994, 116, 395; G. Dranoff, E. Jaffee, A. Lazenby, P. Golumbek, H. Levitsky, K. Brose, V. Jackson, H. Hamada, D. Paardoll, R. Mulligan, Proc. Natl. Acad. Sci. USA 1993, 90, 3539; M-H. Tao, R. Levy Nature 1993, 362, 755; d) T. Boon, Int. J. Cancer 1993, 54, 177; P. O. Livingston, Curr. Opin. Immunol. 1992, 4, 624; S. Hakomori, Annu. Rev. Immunol. 1984, 2, 103; K. Shigeta, Y. Ito, T. Ogawa, Y. Kirihata, S. Hakomori, R. Kannagi, J. Biol. Chem. 1987, 262, 1358)

The present invention provides new strategies and protocols for oligosaccharide synthesis. The object is to simplify such constructions such that relatively complex domains can be assembled with high stereospecifity. Major advances in glycoconjugate synthesis require the attainment of high degrees of convergence and relief from the burdens associated with the manipulation of blocking groups. Another requirement is that of delivering the carbohydrate determinant with appropriate provision for conjugation to carrier proteins or lipids. (M. A. Bernstein, L. D. Hall, Carbohydr. Res. 1980, 78, Cl; R. U. Lemieux, Chem. Soc. Rev. 1978, 7, 423; R. U. Lemieux, D. R. Bundle, D. A. Baker, J. Am. Chem. Soc. 1975, 97, 4076) This is a critical condition if the synthetically derived carbohydrates are to be incorporated into carriers suitable for biological application.

The present invention shows how the use of glycals both as glycosyl donors and as glycosyl acceptors can be exploited to accomplish such ends in the context of a straightforward synthesis of the $Le^y$ (type II) system. The $Le^y$ hapten was first isolated from a blood group glycoprotein in 1966 by Kabat and Lloyd. (K. O. Lloyd, E. A. Kabat, E. J. Layug, F. Gruezo, Biochem. 1966, 5, 1489) Subsequently, Potapov and coworkers (M. I. Potapov, Probl. Hematol. Blood Transfus. (USSR) 1970, 15, 45) discovered an antibody to this carbohydrate antigen. Interest in the $Le^y$ antigen stems from the existence of a number of glycoproteins and glycolipids which contain this substructure and are associated with human colonic adenocarcinoma (T. Kaizu, S. B. Levery, E. Nudelman, R. E. Stenkamp, S. Hakomori, J. Biol. Chem. 1986, 261, 11254) as well as human liver adenocarcinoma. (S. B. Levery, E. Nudelman, N. H. Anderson, S. Hakomori, Carbohydr. Res. 1986, 151, 311) Both $Le^y$ and $Le^x$ antigenic structures are of general interest due to the preponderance of highly fucosylated polylactosamine glycolipids that are found to accumulate in other human carcinomas. (S. Hakomori, Annu. Rev. Immunol. 1984, 2, 103; S. Hakomori, E. Nudelman, S. B. Levery, R. Kannagi, J. Biol. Chem. 1984, 259, 4672; Y. Fukushi, S. Kakomori, E. Nudelman. N. Cochran, ibid. 1984, 259, 4681; Y. Fukushi, E. Nudelman, S. B. Levery, S. Hakomori, H. Rauvala, ibid. 1984, 259, 10511) The method of synthesis disclosed herein provides for the determinant to be insulated from the conjugation device by a carbohydrate spacer module which can in principle be broadly varied. Through appropriate insulation, the likelihood that the protein or lipid carrier might distort the recognition property of the determinant is thus minimized.

Also disclosed herein is the construction of the Lewis[b] determinant. (For alternative methods for synthesizing Le[2] oligosaccharides, see: S. S. Rana, J. J. Barlow, K. L. Matta, *Carbohydr. Res.* 1981, 96, 231; U. Spohr, R. U. Lemieux, *Carbohydr. Res.* 1988, 174, 211) The present invention provides a method of equipping the reducing end of the antigen with a suitable device for subsequent attachment to a carrier protein. An intervening spacer element (lactose) is inc

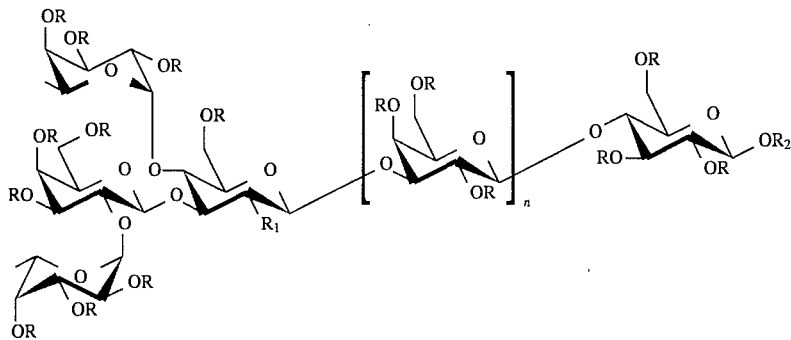

wherein n is an integer from 1 to 18; wherein R is H or a linear or branched chain acyl group; wherein $R_1$ is H, OH, $NH_2$ or $NHR_4$, where $R_4$ is $SO_2Ph$, a linear or branched chain alkyl or acyl group, or an aryl group; and wherein $R_2$ is a substituted or unsubstituted allyl group.

The present invention further provides a compound having the structure:

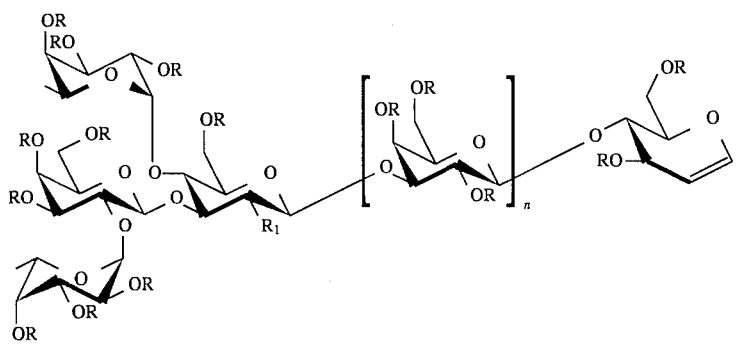

wherein R is H or a linear or branched chain acyl group; wherein $R_1$ is H, OH, $NH_2$ or $NHR_4$, where $R_4$ is $SO_2Ph$, a linear or branched chain alkyl or acyl group, or an aryl group; wherein $R_2$ is a substituted or unsubstituted allyl group; and wherein n is an integer from 1 to 18.

The present invention provides a compound having the structure:

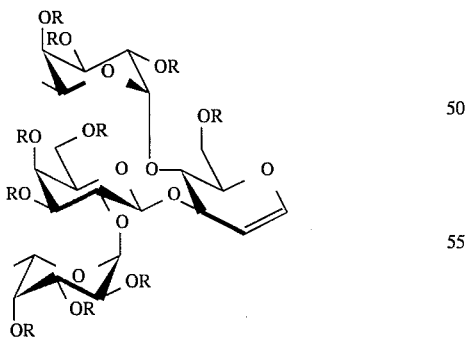

wherein R is H or a linear or branched chain acyl group.

The present invention also provides a process for synthesizing a compound having the structure:

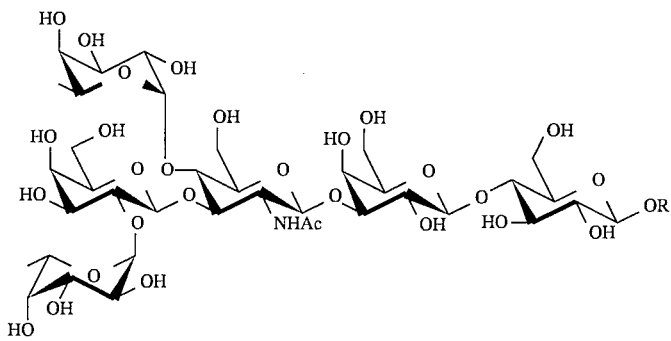

wherein R is a substituted or unsubstituted allyl group.

DETAILED DESCRIPTION OF THE INVENTION

Figure 1:
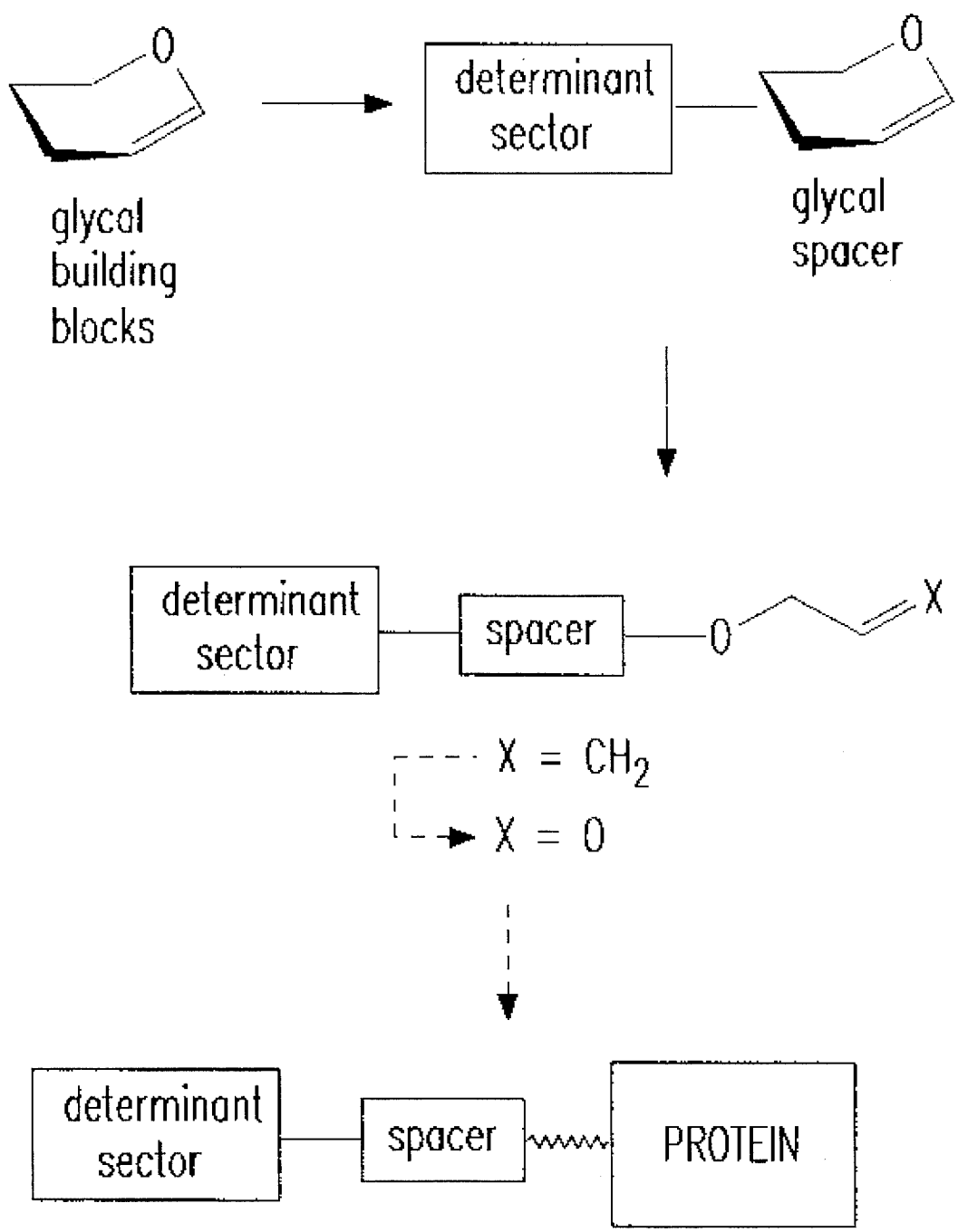
FIG. 1 shows glycal assembly leading to neoglycoproteins.

The present invention provides a compound having the structure:

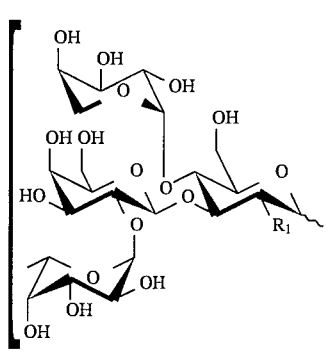

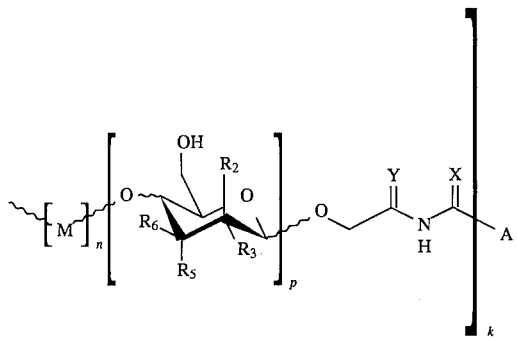

wherein A is selected from the group consisting of (i) an amino acid bearing an ω-amino group or an ω-(C=O)— group, (ii) an amino acid residue of a peptide, which residue bears an ω-amino group or an ω-(C=O)— group, and (iii) an amino acid residue of a protein, which residue bears an ω-amino group or an ω-(C=O)— group; wherein R$_1$ is H, OH, NH$_2$ or NHR$_4$, where R$_4$ is SO$_2$Ph, a linear or branched chain alkyl or acyl group, or an aryl group; wherein M has the structure:

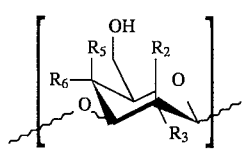

wherein n is an integer from 0 to 18, and where n is greater than 1, each M is independently the same or different; wherein p is either 0 or 1; wherein R$_2$, R$_3$, R$_5$ and R$_6$ are independently the same or different and are H or OH, with the proviso that $R_2$ and $R_3$ are not both OH, and $R_5$ and $R_6$ are not both OH; wherein each wavy line between a carbon atom and an oxygen atom denotes an R or S configuration at the carbon atom; wherein X and Y are independently the same or different and are $H_2$ or O; and wherein k is an integer greater than or equal to 1, with the proviso that when A is an amino acid bearing an ω-amino group or an ω-(C=O)— group, k is equal to 1.

In one embodiment, the present invention provides the compound disclosed hereinabove wherein A is lysine or a lysine residue.

In another embodiment, the present invention provides the compound disclosed hereinabove wherein A is glutamic acid or a glutamic acid residue.

In another embodiment, the present invention provides the compound disclosed hereinabove wherein A is aspartic acid or an aspartic acid residue.

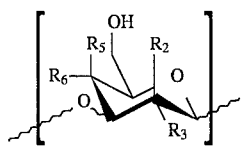

wherein n is an integer from 0 to 18, and where n is greater than 1, each M is independently the same or different; wherein $R_2$, $R_3$, $R_5$ and $R_6$ are independently the same or different and are H or OH, with the proviso that $R_2$ and $R_3$ are not both OH, and $R_5$ and $R_6$ are not both OH; wherein each wavy line between a carbon atom and an oxygen atom denotes an R or S configuration at the carbon atom; and wherein $R_7$ is a substituted or unsubstituted allyl group.

The invention also provides a compound having the structure:

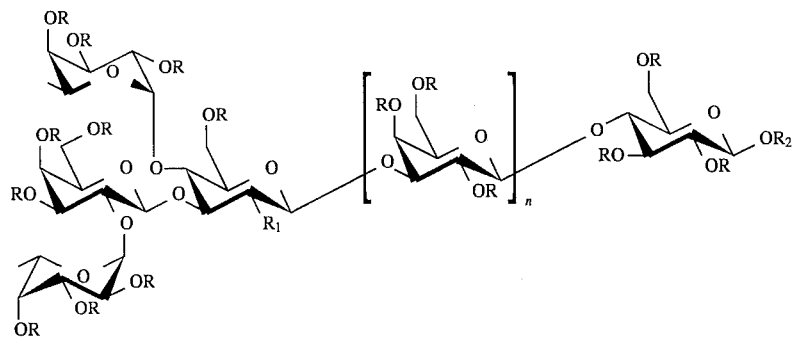

The invention also provides the compound disclosed hereinabove wherein A is an amino acid residue of a globular protein. In one embodiment, the invention provides the compound wherein the globular protein is selected from the group consisting of bovine serum albumin and human serum albumin.

In one embodiment, the invention provides the compound disclosed hereinabove wherein k is 1.

In another embodiment, the invention provides the compound disclosed hereinabove wherein n and p are both equal to 0.

The invention provides a compound having the structure:

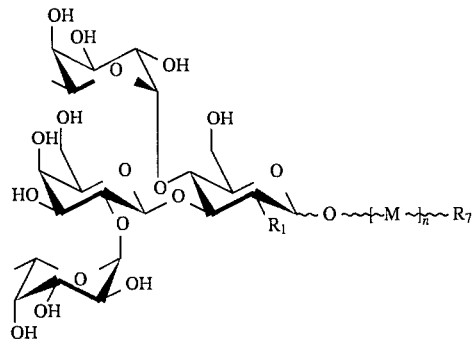

wherein $R_1$ is H, OH, $NH_2$ or $NHR_4$, where $R_4$ is $SO_2Ph$, a linear or branched chain alkyl or acyl group, or an aryl group; wherein M has the structure:

wherein n is an integer from 1 to 18; wherein R is H or a linear or branched chain acyl group; wherein $R_1$ is H, OH, $NH_2$ or $NHR_4$, where $R_4$ is $SO_2Ph$, a linear or branched chain alkyl or acyl group, or an aryl group; and wherein $R_2$ is a substituted or unsubstituted allyl group. In one embodiment, the invention provides the compound wherein n is 1.

The invention further provides a compound having the structure:

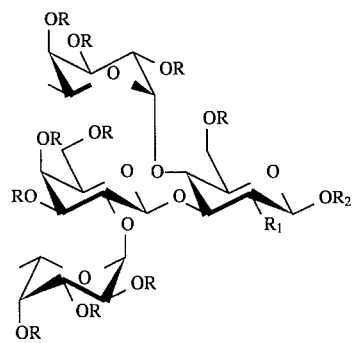

wherein R is H or a linear or branched chain acyl group; wherein $R_1$ is H, OH, $NH_2$ or $NHR_4$, where $R_4$ is $SO_2Ph$, a linear or branched chain alkyl or acyl group, or an aryl group; and wherein $R_2$ is a substituted or unsubstituted allyl group.

The invention also provides a compound having the structure:

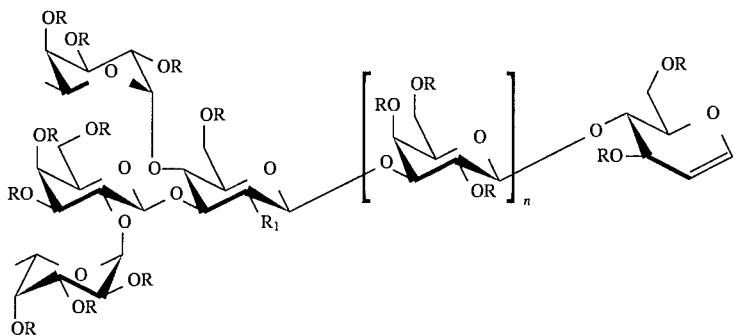

wherein R is H or a linear or branched chain acyl group; wherein $R_1$ is H, OH, $NH_2$ or $NHR_4$, where $R_4$ is $SO_2Ph$, a linear or branched chain alkyl or acyl group, or an aryl group; wherein $R_2$ is a substituted or unsubstituted allyl group; and wherein n is an integer from 1 to 18. In one embodiment, the invention provides the compound wherein n is 1.

The invention also provides a compound having the structure:

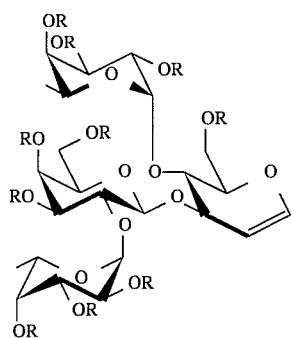

wherein R is H or a linear or branched chain acyl group.

The invention also provides a process for synthesizing a compound having the structure:

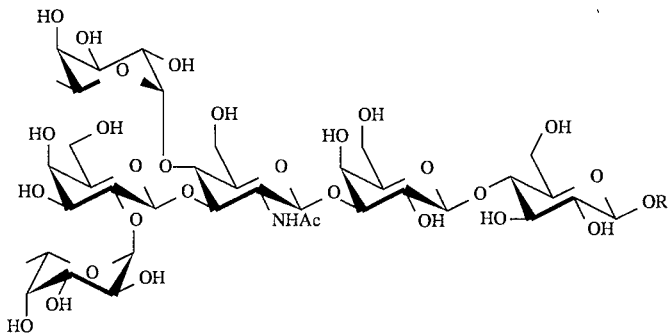

wherein R is a substituted or substituted allyl group, which comprises the steps of (a) synthesizing a compound having the structure:

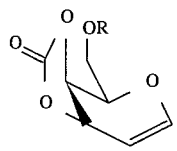

wherein R is a trialkylsilyl, aryldialkylsilyl, alkyldiarylsilyl or triaarylsilyl group; (b) reacting the compound of step (a) with a compound having structure:

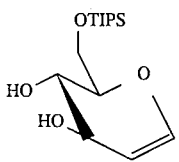

under suitable conditions to form a compound having the structure:

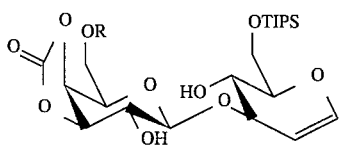

wherein R is a trialkylsilyl, aryldialkylsilyl, alkyldiarylsilyl or triaarylsilyl group; (c) reacting the compound formed in step (b) with a compound having the structure:

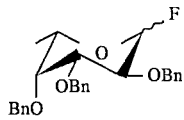

under suitable conditions to form a compound having the structure:

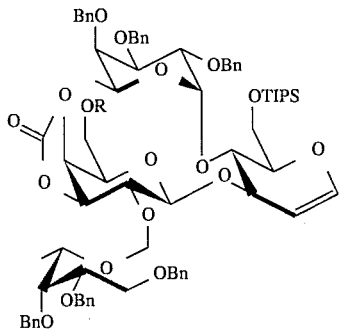

wherein R is a trialkylsilyl, aryldialkylsilyl, alkyldiarylsilyl or triaarylsilyl group; (d) deprotecting and re-protecting the compound formed in step (c) under suitable conditions to form a compound having the structure:

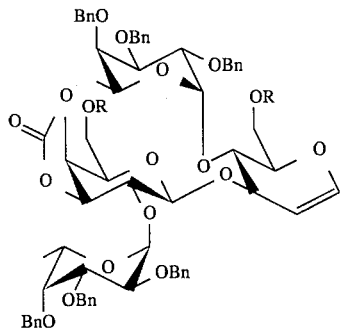

wherein R is TIPS; (e) iodosulfonamidating the compound formed in step (d) under suitable conditions to form a compound having the structure:

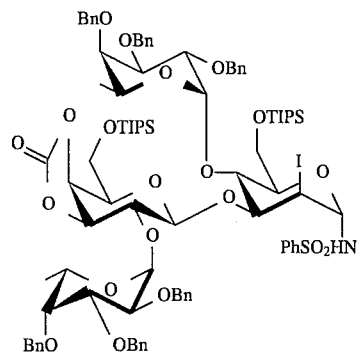

(f) reacting the compound formed in step (e) with a compound having the structure:

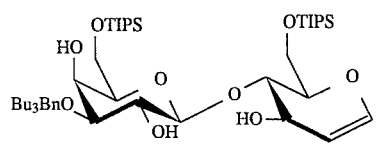

under suitable conditions to form a compound having the structure:

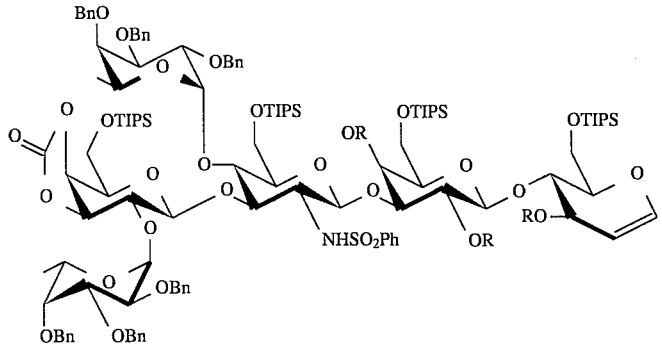

wherein R is H; (g) deprotecting and peracetylating the compound formed in step (f) under suitable conditions to form a compound having the structure:

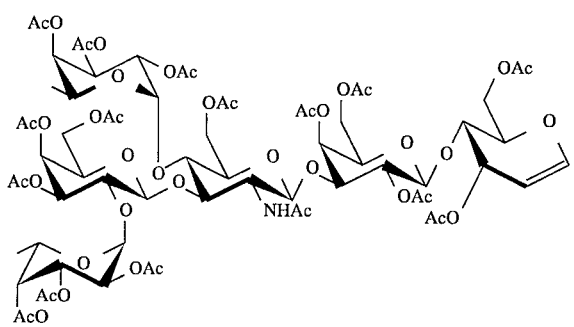

(h) epoxidizing the compound formed in step (g) under suitable conditions to form an epoxide thereof and reacting the epoxide under suitable conditions to form a compound having the structure:

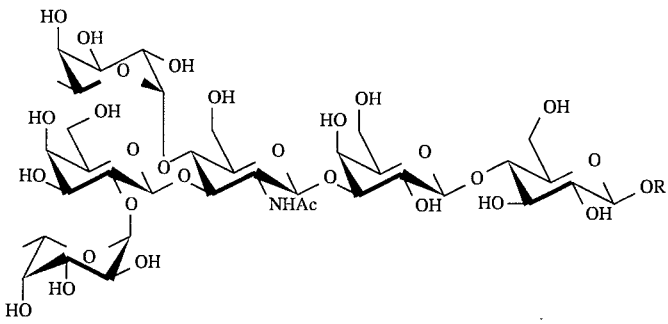

wherein R is a substituted or unsubstituted allyl group; and
(i) treating the compound formed in step (h) under suitable conditions to form a compound having the structure:

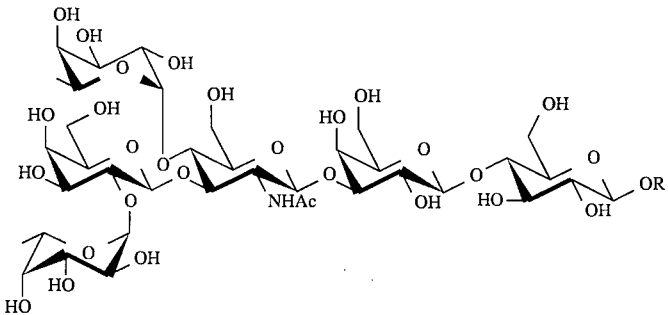

wherein R is a substituted or unsubstituted allyl group. In the above process the suitable conditions necessary for the various reactions and treatments may be found in the Experimental Details section which follows hereinafter. However, it is within the confines of the present invention that the specific reagents and solvents provided as well as the specific conditions necessary for reaction or treatment may be substituted with other suitable reactants, solvents and conditions well known to those skilled in the art.

The allyl compound may be conjugated to a peptide or protein via amine or carboxylic acid side chain. In practicing the invention, a bioconjugate is prepared according to the protocol of Bernstein and Hall (Carbohydr. Res. 1980, 78, C1). The allyl group is ozonolyzed to form either an aldehyde or carboxylic acid, which is condensed to a terminal amine to form, respectively, an imine or an amide. The imine is reduced with sodium borohydride to the amine. Alternatively, the aldehyde is reductively aminated using procedures known in the art to form an amine which is reacted with a side-chain terminal carboxylic acid to form an amide conjugate.

The invention provides a pharmaceutical composition which comprises a therapeutically effective amount of the compound disclosed hereinabove and a pharmaceutically acceptable carrier.

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

The invention further provides a method for treating a subject afflicted with a disorder caused by *Helicobacter pylori* which comprises administering to the subject a therapeutically effective amount of the pharmaceutical composition disclosed hereinabove so as to treat the subject afflicted with the disorder.

In one embodiment, the invention provides a method of treating a subject afflicted with gastric or duodenal ulcer.

In another embodiment, the invention provides a method of treating a subject afflicted with gastric adenocarcinoma.

In addition, the invention provides a method for inhibiting the adhesion of *Helicobacter pylori* to gastric epithelium in a subject which comprises administering to the subject an amount of the compound disclosed hereinabove effective to inhibit the adhesion of *Helicobacter pylori* to gastric epithelium in the subject.

Experimental Details

General Procedures

All air- and moisture-sensitive reactions were performed in a flame-dried apparatus under an argon atmosphere unless otherwise noted. Air-sensitive liquids and solutions were transferred via syringe or canula. Wherever possible, reactions were monitored by thin-layer chromatography (TLC). Gross solvent removal was performed in vacuum under aspirator vacuum on a Buchi rotary evaporator, and trace solvent was removed on a high vacuum pump at 0.1–0.5 mmHg. Melting points (mp) were uncorrected and performed in soft glass capillary tubes using an Electrothermal series IA9100 digital melting point apparatus.

Infrared spectra (IR) were recorded using a Perkin-Elmer 1600 series Fourier-Transform instrument. Samples were prepared as neat films on NaCl plates unless otherwise noted. Absorption bands are reported in wavenumbers (cm$^{-1}$). Only relevant, assignable bands are reported.

Proton nuclear magnetic resonance ($^1$H NMR) spectra were determined using a Bruker AMX-400 spectrometer at 400 MHz. Chemical shifts are reported in parts per million (ppm) downfield from tetramethylsilane (TMS; $\delta$=0 ppm) using residual CHCl$_3$ as a lock reference ($\delta$=7.25 ppm). Multiplicities are abbreviated in the usual fashion: s=singlet; d=doublet; t=triplet; q=quartet; m=multiplet; br=broad.

Carbon nuclear magnetic resonance ($^{13}$C NMR) spectra were performed on a Bruker AMX-400 spectrometer at 100 MHz with composite pulse decoupling. Samples were prepared as with $^1$H NMR spectra, and chemical shifts are reported relative to TMS (0 ppm); residual CHCl$_3$ was used as an internal reference ($\delta$=77.0 ppm).

All high resolution mass spectral (HRMS) analyses were determined by electron impact ionization (EI) on a JEOL JMS-DX 303HF mass spectrometer with perfluorokerosene (PFK) as an internal standard. Low resolution mass spectra (MS) were determined by either electron impact ionization (EI) or chemical ionization (CI) using the indicated carrier gas (ammonia or methane) on a DelsiNermag R-10-10 mass spectrometer. For gas chromatography/mass spectra (GCMS), a DB-5 fused capillary column (30 m, 0.25 mm thickness) was used with helium as the carrier gas. Typical conditions used a temperature program from 60°–250° C. at 40° C./min.

Thin layer chromatography (TLC) was performed using precoated glass plates (silica gel 60, 0.25 mm thickness). Visualization was done by illumination with a 254 nm UV lamp, or by immersion in anisaldehyde stain (9.2 mL p-anisaldehyde in 3.5 mL acetic acid, 12.5 mL conc. sulfuric acid and 338 mL 95% ethanol (EtOH)) and heating to colorization.

Flash silica gel chromatography was carried out according to the standard protocol.

Unless otherwise noted, all solvents and reagents were commercial grade and were used as received, except as indicated hereinbelow, where solvents were distilled under argon using the drying methods listed in parethenses: CH$_2$Cl$_2$ (CaH$_2$); benzene (CaH$_2$); THF (Na/ketyl); Et$_2$O (Na/ketyl); diisopropylamine (CaH$_2$).

| Abbreviations | |
|---|---|
| OTf | triflate |
| M.S. | molecular sieves |
| TLC | thin layer chromatography |
| EtOAc | ethyl acetate |
| TIPS | triisopropylsilyl |
| Bn | benzyl |
| Ac | acetate |
| hex | hexane |
| THF | tetrahydrofuran |
| coll | collidine |
| r.t. | room temperature |
| r.b. | round bottom flask |

EXAMPLE 1

Preparation of Polymer-Bound Glucal 18

Polymer-bound galactal 7 (500 mg; S. J. Danishefsky, et al., J. Am. Chem. Soc. 1992, 8331) was placed in a 100 mL polymer flask and dried in vacuo. On cooling to 0° C. under N$_2$; dry CH$_2$Cl$_2$ (20 mL) and freshly prepared Murray solution (30 mL; R. W. Murray and R. Jeyaraman, J. Org Chem. 1985, 2847) was added. After stirring at 0° C. for ~90 min., solubles were filtered using N$_2$ pressure. The oxidation procedure was repeated. The resulting epoxide of 7 kept on a vacuum line for ~3 h to dry. A solution of glucal 19 (1.0 g in 8 mL dry THF) was added, and the mixture was cooled to –23° C. (dry ice-CCl$_4$). A solution of ZnCl$_2$ in THF (0.8 mL 1.0M) was added. The mixture was slowly allowed to warm to r.t. (over ~2 h), and then stirred at r.t. overnight. The polymer-bound glucal 18 was rinsed with 3×20 mL THF, and dried on a vacuum line.

Preparation of Polymer-Bound Tetrasaccharide 20

Polymer-bound glucal 18 and Sn(OTf)$_2$ (0.80 g, 1.92 mmol) were combined and dried in vacuo. On cooling to 0° C. under N$_2$, a solution of fucosyl donor 10 (1.8 g, 4.1 mmol) in 20 mL dry THF with di-t-butylpyridine (1.7 mL, 7.57 mmol) was added. The mixture was allowed to warm slowly to r.t., and stirred overnight. The polymer was washed with 2×20 mL dry THF, 2×20 mL dry dioxane, 20 mL DMSO, and 2×20 mL THF. The resulting polymer-bound tetrasaccharide 20 was kept on a vacuum line to dry.

Preparation of Tetrasaccharide Glycal 21

The polymer-bound tetrasaccharide 20 (50 mg) was stirred in 2 mL THF, and treated with 0.2 mL each of 1.0M solutions of TBAF and AcOH in THF. The mixture was stirred at 40° C. overnight. The polymer was washed with 3×5 mL THF. The combined rinsings were concentrated and column-chromatographed on silica (2:1 EtOAc:hex), providing tetrasaccharide glycal 21 as a colorless gum. Yield: 9.0 mg.

EXAMPLE 2

Preparation of Diol 18'

Galactal 7' (0.100 g, 0.304 mmol) in 5 mL dry CH$_2$Cl$_2$ at 0° C. under a N$_2$ atmosphere was treated with 10 mL Murray solution (freshly prepared) and stirred at 0° C. for 40 min. TLC (1:1 EtOAc:hex) showed no trace of 7'. Solvents were evaporated using a dry N$_2$ stream. The residual epoxide of 7' was kept on a vac. line ~2h. To the epoxide under a N$_2$ atmosphere was added a solution of glucal derivative 3'

(0.150 g, 0.496 mmol) in 3 mL dry THF. On cooling to −78° C., 1.0M ZnCl$_2$ in Et$_2$O (0.50 mL, 0.50 mmol) was added. The mixture was allowed to slowly warm to r.t. (over ~2 h) and stirred overnight. TLC (1:1 EtOAc:hex) showed that the reaction was complete. Saturated aq. NaHCO$_3$ (20 mL) was added, and the mixture was then extracted with EtOAc (3×20 mL). The organic layer was dried over MgSO$_4$. Column chromatography on silica (1:3 EtOAc:hex) afforded diol 18' as a colorless solid. Yield: 173 mg (89%). [α]$_D^{23}$=−9.8° (c 1.0, CH$_2$Cl$_2$).

Preparation of Tetrasaccharide 22

Diol 18' (86 mg, 0.133 mmol) and fucosyl donor 10 (0.290 g, 0.665 mmol) were azeotropically dried using benzene. The mixture was dissolved in 3 mL dry THF together with 0.65 mL di-t-butylpyridine and then added via canula to a flask containing Sn(OTf)$_2$ (0.30 g, 0.72 mmol) and 4 Å MS (500 mg) at 0° C. under N$_2$ atm. The mixture was stirred at 0° C. ~7 h. TLC (1:3 EtOAc:hex) shows no trace of diol 18'. The mixture was partitioned between saturated aq. NaHCO$_3$ (100mL) and EtOAc (2×100mL). The organic layer was dried over MgSO$_4$. The organic layer was filtered through silica using EtOAc to obtain crude material, which was then purified by chromatography on silica (1:9 EtOAc:hex) affording tetrasaccharide 22. Yield: 170 mg (86%).

Preparation of Iodosulfonamide 23

Procedure 1.

Tetrasaccharide glycal 22 (120 mg, 81.1 mmol) and PhSO$_2$NH$_2$ (20 mg, 0.13 mmol) were azeotropically dried using benzene. Added (glove bag) 4 Å MS (0.2 g). After cooling to 0° C. under N$_2$, dry CH$_2$Cl$_2$ (1.0 mL) was added. The mixture was treated with a solution of I(coll)$_2$ClO$_4$ (prepared from 100 mg Ag(coll)$_2$ClO$_4$, 5 mL collidine, and 60 mg I$_2$ in 1 mL dry CH$_2$Cl$_2$) via canula through a plug of flame-dried celite and 4 Å MS. The mixture was stirred at 0° C. for 40 min. TLC (1:4 EtOAc:hex) showed iodosulfonamide 23 as the major component. The mixture was filtered through celite, which was rinsed with Et$_2$O. The organic layer was extracted with saturated aq. Na$_2$S$_2$O$_3$, saturated aq. CuSO$_4$, brine, and then dried over MgSo$_4$. Column chromatography on silica (1:4 EtOAc:hex) gave iodosulfonamide 23 as a colorless solid. Yield: 115 mg (80%).

Procedure 2.

Tetrasaccharide glycal 22 (200 mg, 0.135 mmol), PhSO$_2$NH$_2$ (42 mg, 0.27 mmol), and 200 mg powdered 4 Å MS in 2.0 mL dry CH$_2$Cl$_2$ at 0° C. under a N$_2$ atmosphere was treated with I(coll)$_2$ClO$_4$ (prepared from 120 mg Ag(coll)$_2$ClO$_4$ and 67 mg I$_2$ in 1 mL dry CH$_2$Cl$_2$). The mixture was stirred at 0° C. (protected from light using foil) for 30 min. TLC (1:2 EtOAc:hex) showed mainly iodosulfonamide with some glycal.

After ~1 h more at 0° C., TLC showed no noticeable improvement. The mixture was filtered through celite, which was washed with Et$_2$O. After extracting with saturated aq. Na$_2$S$_2$O$_3$, saturated aq. CuSO$_4$, brine, the organics were dried over MgSO$_4$. Column chromatography on silica (1:3 EtOAc:hex) gave 23 as a colorless solid. Yield: 165 mg (69%). [α]$_D^{23}$=−85.7° (c 1.0, CH$_2$Cl$_2$).

Preparation of Hexasaccharide 25

Iodosulfonamide 23 (60 mg, 34 mmol) in a 35 mL r.b. was treated with 200 mg powdered 4 Å MS (glove bag). To this flask under N$_2$ was added a solution of protected lactal 24 in THF (1.5 mL). On cooling the mixture to −78° C., a solution of AgBF$_4$ (40 mg, 0.206 mmol) was added in 0.25 mL dry THF. The mixture was stirred and slowly warmed to r.t. overnight. The mixture was warmed to 45° C. and stirred ~36 h. TLC showed only a trace of iodosulfonamide. Saturated aq. NH$_4$Cl (5 mL) was added, and extracted with 3×10 mL EtOAc. The organic layer was dried over MgSO$_4$. Column chromatography on silica (1:3 EtOAc:hex) afforded 25 as a colorless oil. Yield: 42 mg (55%). [α]$_D^{23}$=−33.8° (c 2.0, CH$_2$Cl$_2$)

Preparation of Hexasaccharide 25a

Hexasaccharide 25 (55 mg, 24.4 mmol) in ~1.5 mL THF was treated at 0° C. with TBAF (0.25 mL, 1.0M solution in THF, 0.25 mmol), and stirred at r.t. overnight. TLC (1:9 MeOH:CH$_2$Cl$_2$) showed a 3:1 mixture of 25a vs. a less polar substance. Additional 1.0M TBAF (0.10 mL) was added, and the mixture was stirred overnight at r.t. TLC showed that the reaction was complete. Solvents were removed using a N$_2$ stream. Column chromatography on silica (1:19 MeOH:CH$_2$Cl$_2$) afforded a ~1:2 mixture corresponding to two compounds which differ only in the presence or absence of a 3,4-cyclic carbonate group. Crude yield: 35 mg total weight for two products. The crude mixture was used as such for the next reaction.

Preparation of Peracetylated Hexasaccharide 26

Hexasaccharide 25a (36 mg) in 0.25 mL dry THF was added via canula to ~8 mL bright blue Na/NH$_3$ solution at −78° C. (dry ice bath) under N$_2$ atm. After removing the dry ice bath, the mixture was stirred in refluxing NH$_3$ (dry ice condenser) for 15 min. After adding 2 mL dry MeOH (slowly!), the resulting mixture was stirred while blowing off NH$_3$ with a N$_2$ stream. The MeOH solution was treated with Dowex 50×8 [H$^+$] until pH ~8–9, and then filtered. The resin was washed with MeOH. The residue was concentrated and kept on a vacuum line to dry. Under a N$_2$ atmosphere, the residue was treated with 1 mL dry pyridine and 0.5 mL Ac$_2$O, and stirred at r.t. overnight. TLC (EtOAc) showed that hexasaccharide 26 is major component. Upon concentration, the residue was purified by column chromatography on silica (1:4 hex:EtOAc).

Preparation of Hexasaccharide 17

Hexasaccharide 26 (10.0 mg, 6.3 mmol) under N$_2$ at 0° C. was treated with 0.5 mL dry CH$_2$Cl$_2$. Dioxirane solution (0.20 mL) was added, and the mixture was stirred at 0° C. ~40 min. TLC (EtOAc) showed no trace of 26. Solvents were evaporated with a N$_2$ stream. The epoxide was dried on a vacuum line for ~2 h. The epoxide was treated under a N$_2$ atmosphere with 0.5 mL allyl alcohol (passed through basic alumina to dry) and 0.5 mL dry THF. On cooling to −78° C., 1.0M ZnCl$_2$ (10 mL) in dry Et$_2$O was added. After warming slowly to r.t., the mixture was stirred overnight. Saturated aq. NaHCO$_3$ (5mL) was added, and the mixture was extracted with 3×5 mL EtOAc. The combined organic layers were dried over MgSO$_4$, filtered and concentrated to an oil, which was dried on a vacuum line for ~2 h. The residue was treated to pyridine:Ac$_2$O (2:1, 1.5 mL) while stirring overnight. Solvents were removed, and the residue was purifed by column chromatography on silica (1:4 hex:EtOAc), affording hexasaccharide 17 as a colorless solid. Yield: 5.5 mg.

Results and Discussion

Figure 2:
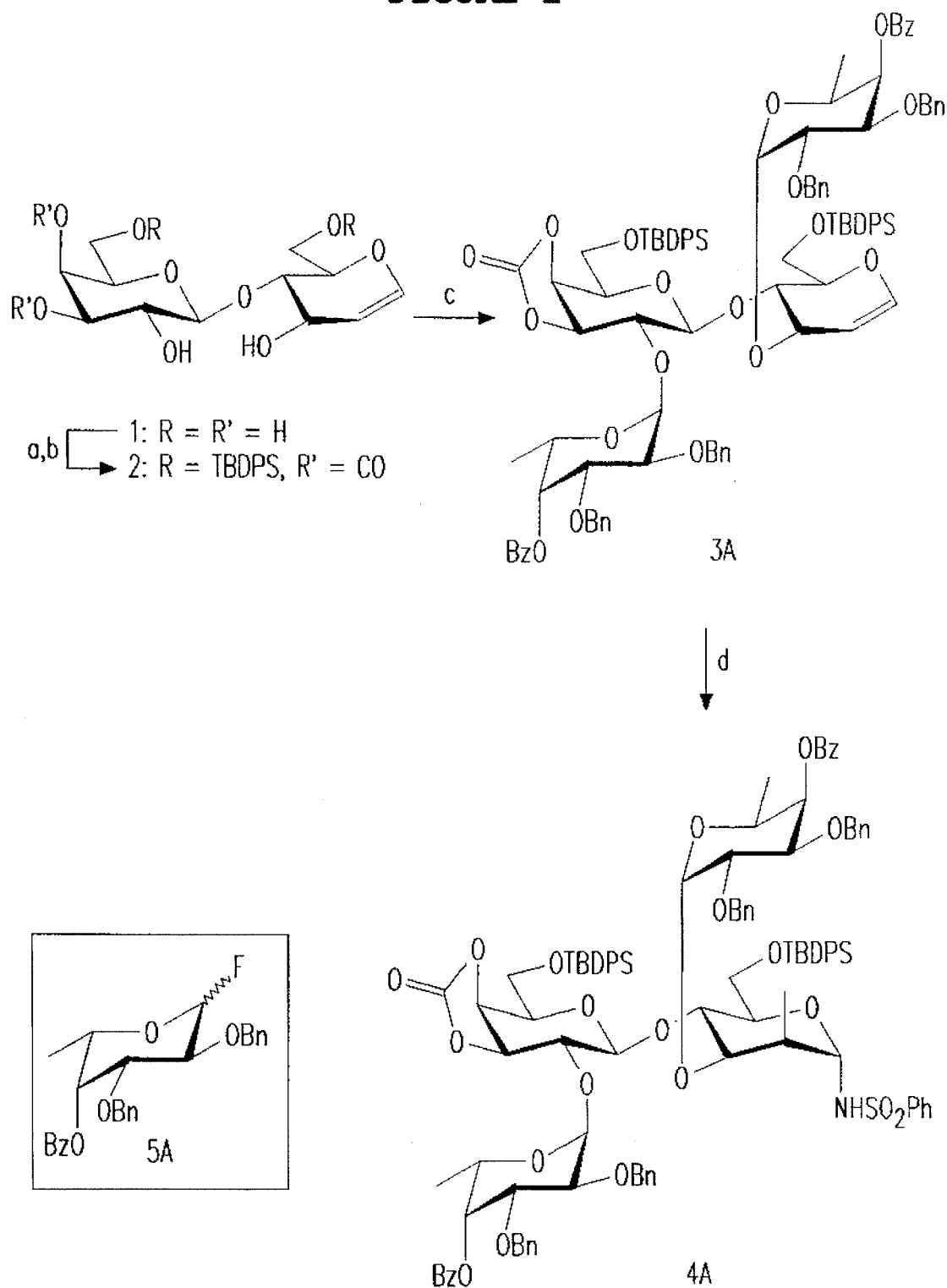
FIG. 2 shows the synthesis of 4a. Reagents: a) TBDPSCL, imidazole/DMF 84%; b) carbonyldiimidazole, cat. imidazole, THF (65%) c) 5a, di-tert-butylpyridine, AgClO$_4$, SnCl$_2$, ether (51%); PhSO$_2$NH$_2$, 1(sym-coll)$_2$ClO$_4$ (94%).

A Highly Convergent Synthesis of the Lewis Y Blood Group Determinant in Conjugatable Form Construction of the Le$^y$ determinant commences with lactal (1a) (W. N. Haworth, E. L. Hirst, M. M. T. Plant, R. J. W. Reynolds, *J. Chem. Soc.* 1930, 2644) as shown in FIG. 2. Capping both primary hydroxyl groups as their TBDPS ethers under standard conditions was followed by simple engagement of the 3' and 4' hydroxyl functions as a cyclic carbonate 2a. The stereospecific introduction of two α-linked fucose residues gave tetrasaccharide glycal 3a in 51% yield in a single step. The donor used was the known fluorosugar 5a (S. J. Danishefsky, J. Gervay, J. M. Peterson, F. E. McDonald, K. Koseki, T. Oriyama, D. A. Griffith, C-H. Wong, D. P. Dumas, *J. Am. Chem. Soc.* 1992, 114, 8329) following a modification of the original Mukaiyama conditions. (T. Mukaiyama, Y. Murai, S. Shoda, Chem. Lett. 1981, 431) Glycal 3a corresponds to the Le$^y$ hapten, lacking the N-acetyl function in the glucose residue. The problem was then to introduce this group as well as a galactose spacer module.

Figure 3:
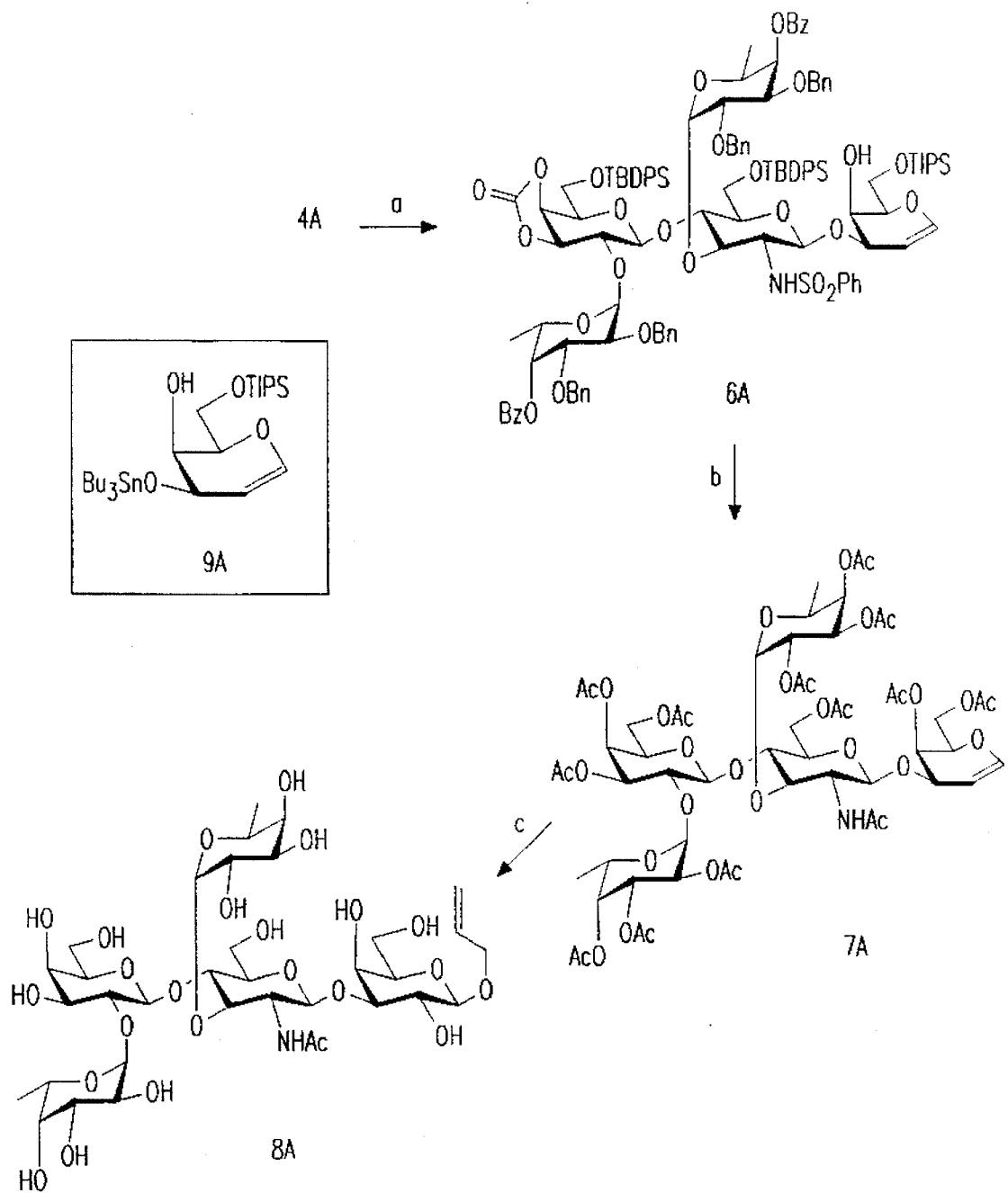
FIG. 3 shows the synthesis of 8a. Reagents: a) 9a, AgBF$_4$, 4A mol. sieves, THF (75%); b) i. TBAF, THF; ii. Na/NH$_3$; iii Ac$_2$O, pyr. c) i. 3,3-dimethioxirane; allyl alcohol, ZnCl$_2$ (72%); ii. NaOMe, MeOH (quant.).

Methodology developed previously (D. A. Griffith, S. J. Danishefsky, "On the Sulfonamidoglycosylation of Glycals. A Route to Oligosaccharides With 2-Aminohexose Subunits+", *J. Am Chem. Soc* 1990 112, 5811) proved appropriate to attain these goals. Glycal 3a was treated with iodonium dicollidine perchlorate and benzenesulfonamide to afford iodosulfonamide 4a. Azaglycosylation using the 3-stannyl ether of galactal (9a) (S. J. Danishefsky, K. Koseki, D. A. Griffith, J. Gervay, J. M. Peterson, F. E. McDonald, T. Oriyama, *J. Am. Chem. Soc.* 1992, 114, 8331) in the presence of silver tetrafluoroborate gave pentasaccharide glycal 6a in 75% yield as shown in FIG. 3. Having 6a in hand, one can iterate the azaglycosylation sequence or activate the glycal as its epoxide and continue with further glycosylations. To demonstrate the ability to fashion a conjugatable form of Le$^y$ hapten, formation of the allyl glycoside was important. The feasibility of converting the sulfonamido group into the target acetamide was demonstrated. Glycal 6a was deprotected in two steps as shown. Peracetylation afforded acetamido glycal 7a. Activation of the glycal as its epoxide with dimethyldioxirane (R. L. Halcomb, S. J. Danishefsky, *J. Am. Chem. Soc.* 1989, 111, 6661), followed by epoxide opening with allyl alcohol in the presence of zinc chloride gave the desired peracetylated β-allyl pentasaccharide which was deacetylated by action of methoxide to provide the target Le$^y$ hapten as its β-allyl glycoside 8a. (8a [α]$_D$–72.7° (c. 1 MeOH); IR (thin film) 3350, 2940, 2900, 2830, 1650, 1550, 1365, 1300, 1155, 1070, 1030; $^1$H NMR (400 MHz, CD$_3$OD) ≠5.95 (m, 1H), 5.32 (d, J=17.25 Hz, 1H), 5.14–5.19 (m, 2H), 5.04 (d, J=3.83 Hz, 1H), 5.02 (d, J=3.50 Hz, 1H). 4.68 (d, J=8.15 Hz, 2H), 4.51 (d, J=5.70 Hz, 1H) 3.40–4.38 (m, 27H). 1.96 (s, 3H), 1.23 (m, 6H); HRMS (FAB) cald for C$_{35}$H$_{56}$NO$_{24}$Na 900.3325 found 900.3310) The aldehyde, derived by ozonolysis of 8a, could be conjugated to a carrier protein by the method of Bernstein and Hall.

This synthesis is the most direct route to the Le$^y$ determinant known. (O. Hindsgaul, T. Norberg, J. Le Pendu, R. U. Lemieux, *Carbohydr Res.* 1982, 109, 109; U. Spohr, R. U. Lemieux ibid, 1988, 174, 211; for previous syntheses, see: J. C. Jacquinet, P. Sinay, *J. Org. Chem.* 1977, 42, 720; S. Nilsson, H. Lohn, T. Norberg, *Glycoconjugate J.* 1989, 6, 21; R. R. Schmidt, A. Topfer, *Tetrahedron Lett.* 1991, 32, 3353; W. Kinzy, A. Low, *Carbohydrate. Res.* 1993, 245, 193) The method is stereospecific at each step, and it illustrates the versatility of glycals both as donors and acceptors and takes advantage of 1,2-glycal epoxides and their presumed N-sulfonylaziridine counterparts. The method also makes possible extensive analog preparation and variation of conjugation strategies.

The synthesis of 3a and 6a are shown below:

3a: To 2.00 g (2.47 mmol) of lactal carbonate 2a was added 4.44 g (9.86 mmol) of fucosyl fluoride 5a. The mixture was azeotroped 5 times with benzene and placed under high vacuum for two hours. Under an argon atmosphere 2.77 ml (12.33 mmol) of di-tert-butyl pyridine and 16 ml of dry ether were added. 2.0 g of freshly activated 4A molecular sieves were added and the mixture stirred one hour at room temperature. In an argon glove bag, 2.34 g (12.33 mmol) of stannous chloride (SnCl$_2$) and 2.56 g (12.33 mmol) of silver perchlorate (AgClO$_4$) were added. The flask was equipped with a reflux condensor and the reaction brought to reflux for 72 hours. The reaction was quenched with 5 ml of saturated bicarbonate and filtered through a pad of celite. Diluted with 50 ml ethyl acetate and washed 2 times with sat. bicarbonate, 2 times with sat. copper sulfate and 2 times with sat. brine. The organics were dried over MgSO$_4$ and concentrated. Flash chromatography in 20% ethyl acetate/hexanes afforded 2.10 g (51%) of a white foam 3a: [α]$_D$–78.9 (c.555,CHCl$_3$); IR (thin film) 3040, 3000, 2905, 2860, 2830, 1820, 1800, 1710, 1635, 1585, 1570, 1480, 1460, 1440, 1415, 1370, 1350, 1300, 1260, 1205, 1145, 1100, 950, 735, 695, $^1$H NMR (400 MHz,CDCl$_3$) δ8.09 (d, J=8.12 Hz, 2H) 8.00 (d, J=8.26 Hz, 2H) 7.66 (m, 4H), 7.59 (d=J=6.74 Hz, 4H), 7.56 (t, J=7.27 Hz, 1H), 7.30–7.50 (m,22H) 7.16–7.26 (m,10H) 7.09 (m,2H), 6.99 (t, J=7.59 Hz, 2H) 6.89 (t, J=7.97 Hz, 1H), 6.43 (d, J=6.08 Hz, 1H), 5.46 (bs, 1H), 5.38 (bs, iH), 5.35 (d, J=3.42 Hz, 1H), 4.89 (d, J=11.35 Hz, 1H), 4.75–4.80 (m, 4H), 4.72 (d, J=5.88 Hz, 2H), 4.69 (d, J=4.27 Hz, 2H), 4.36–4.55 (m, 5H), 4.28 (q, J=6.51 Hz, 1H), 4.17 (bd, J=5.46 Hz, 1H),3.90–4.00 (m,6H), 3.85 (d, J=2.99 Hz, 1H), 3.82 (d, J=2.89 Hz, 1H), 3.56–3.78 (m, 4H), 1.07 (m, 24H); HRMS (FAB): calcd for C$_{99}$H$_{106}$O$_{20}$Si$_2$Na 1694.6740 found 1694.6787.

6a: 230 mg (0.12 mmol) of iodosulfonamide 4a was azeotroped 5 times with dry benzene and placed under high vacuum for two hours. Added 2.4 ml of THF solution of 15 eq. of tin ether 9a (generated by azeotrophic removal of water overnight with a Dean-Stark trap equipped with freshly activated 4A mol. sieves from 561 mg (1.80 mmol) of 6a-TIPS-galactal and 673 µl (1.32 mmol) bis(tributylin)oxide in 80 ml of benzene). To this solution stirring under an argon atmosphere was added 200 mg of freshly activated 4A powdered molecular sieves. Stirred one hour at room temperature. Cooled solution to −78° C. and added, via cannula, a solution of 187 mg (0.96 mmol) of silver tetrafluroborate in 2.4 ml of THF. Warmed to room temperature over 15 hours and quenched the reaction, which had turned bright yellow, with 2 ml. of sat. bicarbonate. The reaction mixture was filtered through a pad of celite into a separatory funnel. The celite pad was washed thoroughly with ethyl acetate. The organics were washed twice with sat. bicarbonate and twice with sat. brine. The organics were dried over MgSO$_4$. Concentration and chromatography in 25% ethyl acetate/hexanes gave 193 mg (75%) as a white foam 6a: [α]$_D$–126.4° (c,505,CHCl$_3$), IR (thin film) 3500, 3040, 3000, 2905, 2840, 1820, 1800, 1705,1635, 1590, 1440, 1410, 1255, 1195, 1100, 1080, 1035, 815, 730, 695; $^1$H NMR (400 MHz, CDCl$_3$) δ8.09 (app t, 4H), 7.08–7.65 (m, 46H), 6.90 (t, J=7.65 Hz, 3H), 6.76 (d, J=6.91 Hz, 2H), 6.12 (d, J=6.59 Hz, 1H), 5.50 (bs 1H), 5.45 (bs 1H), 5.28 (app t, 2H), 3.03–4.91 (m, 36H), 1.09 (m,45H); LRMS (FAB): cald for C$_{120}$H$_{141}$NO$_{26}$SSi$_3$Na 2153 found 2153.

A Strategy for the Assembly of Complex, Branched Oligosaccharide Domains on a Solid Support: An Application to a Concise Synthesis of the Lewis$^b$ Domain in Bioconjugatable Form.

Figure 4:
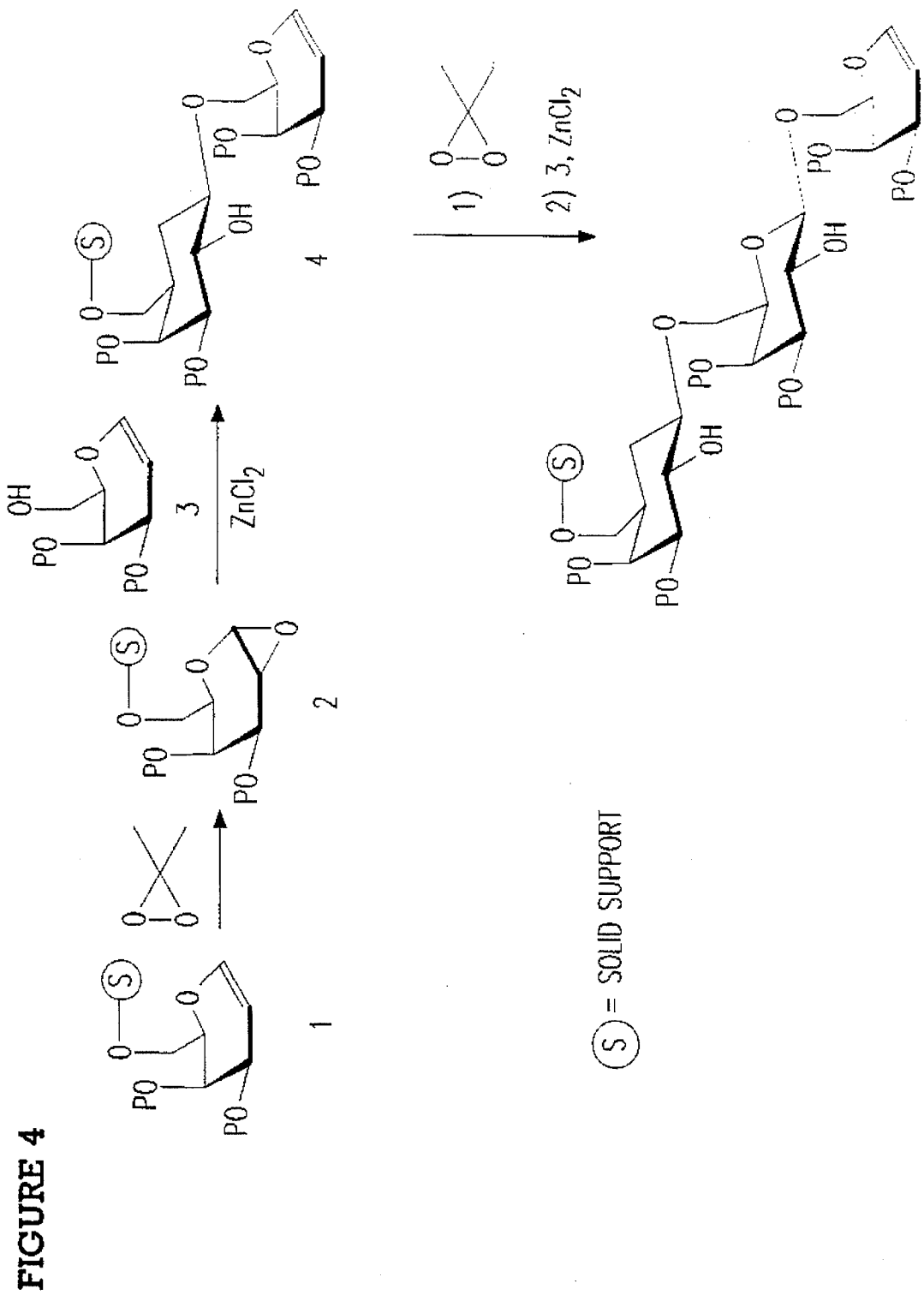
FIG. 4 shows a strategy for the solid-phase of oligosaccharides using the glycal assembly method.

The assembly of the Le$^b$ (type 1) domain is a relatively more difficult undertaking than was the Le$^y$ (type 2) target, wherein lactal was used as a convenient starting material. In the case of the type 1 determinant, lactal is not a useful starting material. The synthesis of the Le$^b$ system offered an opportunity to apply the polymer-based oligosaccharide construction method. (S. J. Danishefsky, K. F. McCLure, J. T. Randolph, R. B. Ruggeri, Science 1993, 260, 1307) The strategy is summarized in FIG. 4, wherein polymer-bound glycal 1 is activated for glycosyl donation via direct formation of a 1,2-anhydro derivative 2. Reaction of 2 with acceptor glycal 3 furnishes 4. Reiteration is achieved by means of direct epoxidation and reaction with acceptor 3. The self-policing nature of the method and the simple "one time" purification at the end of the synthesis are useful features.

Figure 5:
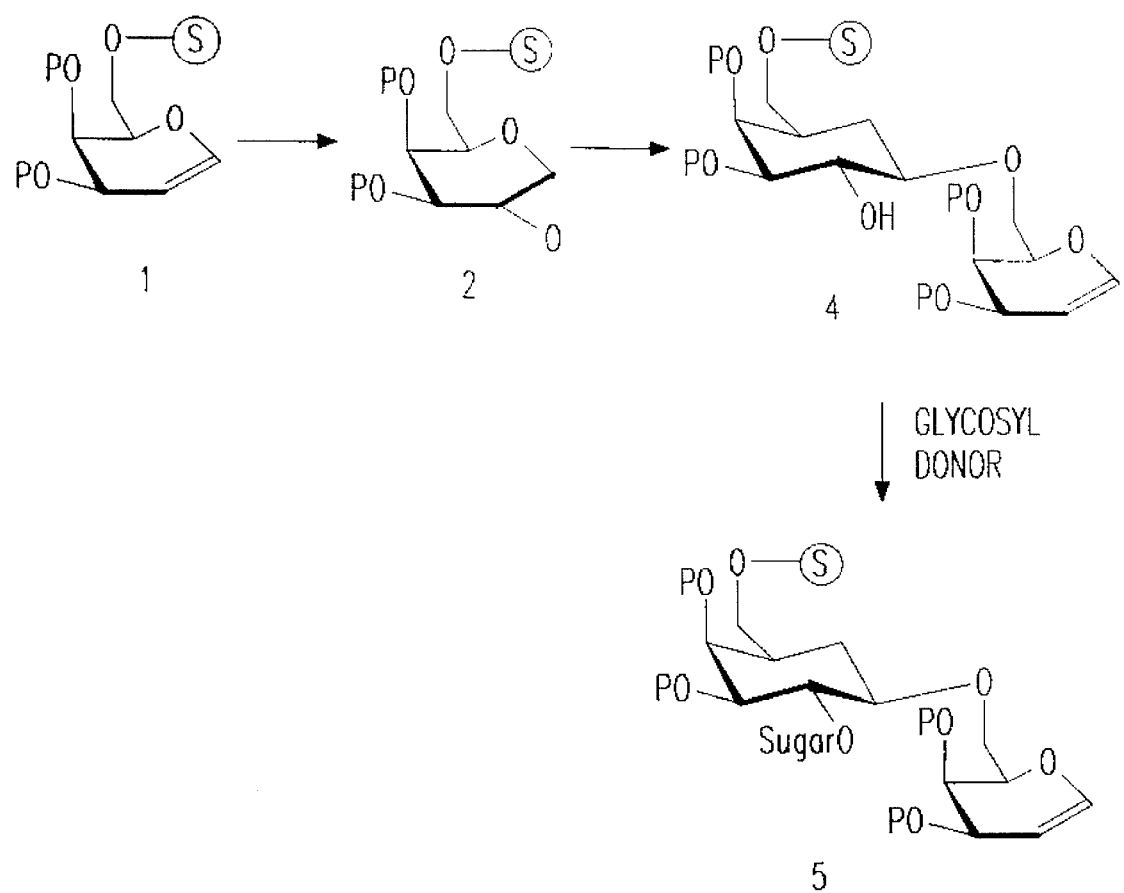
FIG. 5 shows the application of the solid-support method to the assembly of 1,2-branching patterns of complex carbohydrates.

The present invention discloses an important additional dimension of the polymer-bound method. The logic is captured by inspection of FIG. 5. Each glycosylation event generates a unique $C_2$ hydroxyl. In principle (and in fact, see infra) this hydroxyl can function as a glycosyl acceptor upon reaction with a solution based donor. The glycal linkage of 5, still housed on the support, can be further elongated. In this way, branching at $C_2$ is accomplished while minimizing the requirement for protecting group machinations. (For an application of this strategy in the synthesis of a complex saponin, see: J. T. Randolph, S. J. Danishefsky, J. Am Chem Soc. 1993, 115, 8473)

In principle, this branching can be implemented at any site in a growing chain. For such an extension, it would be necessary to cap all previously generated hydroxyl groups generated on the "polymer side" (non-reducing end) of the growing domain. Thus, the polymer-bound oligosaccharide can serve as either donor or acceptor, wherever appropriate.

Initial efforts at reduction to practice identified tetrasaccharide glycal 6, bearing H-type 2 blood group specificity, as a goal. Polymer-supported galactal 7 (using as polymer support polystyrene crosslinked with 1% divinylbenzene functionalized using published procedures: T-H. Chan, W.-Q. Huang, J. Chem. Soc., Chem. Commun. 1985, 909; M. J. Farrall. J. M. J. Frechet, J. Org. Chem 1976, 41, 3877) reacted with a solution of 3,3-dimethyldioxirane (R. W. Murray, R. Jeyaraman, J. Org. Chem. 1985, 50, 2847), to provide the corresponding 1,2-anhydrosugar glycosyl donor, which was treated with a solution of glucal derivative 8 in the presence of $ZnCl_2$ to provide 9 (R. L. Halcomb, S. J. Danishefsky, J. Am. Chem Soc. 1989, 111, 6661) This polymer-bound disaccharide acted as a glycosyl acceptor upon treatment with a solution of fucosyl fluoride 10 (K. C. Nicoloau, C. W. Hummel, Y. Iwabuchi, J. Am. Chem. Soc. 1992, 114, 3126) in the presence of $Sn(OTf)_2$ thereby giving 11. Retrieval of the trisaccharide glycal from the support was accomplished using tetrabutylammonium fluoride (TBAF) to afford 12 in 50% overall yield from 7.

The trisaccharide, retrieved from the polymer, could then be further elaborated. Toward this end, compound 12 was converted to silyl ether 13 by reaction with TIPSCl. The latter was converted to the iodosulfonamide derivative 14 by the action of $I(coll)_2ClO_4$ in the presence of $PhSO_2NH_2$. Reaction of 14 with galactal stannyl ether derivative 15 in the presence of $AgBF_4$ gave 16 77% yield. (D. A. Griffith, S. J. Danishefsky, J. Am. Chem Soc. 1990, 112, 5811) Tetrasaccharide glycal 16 was deprotected and peracetylated to afford 6. (S. J. Danishefsky, K. Koseki, D. A. Griffith, J. Gervay, J. M. Peterson, F. E. MsDonald, T. Oriyama, J. Am. Chem Soc. 1992, 114, 8331)

Figure 6:
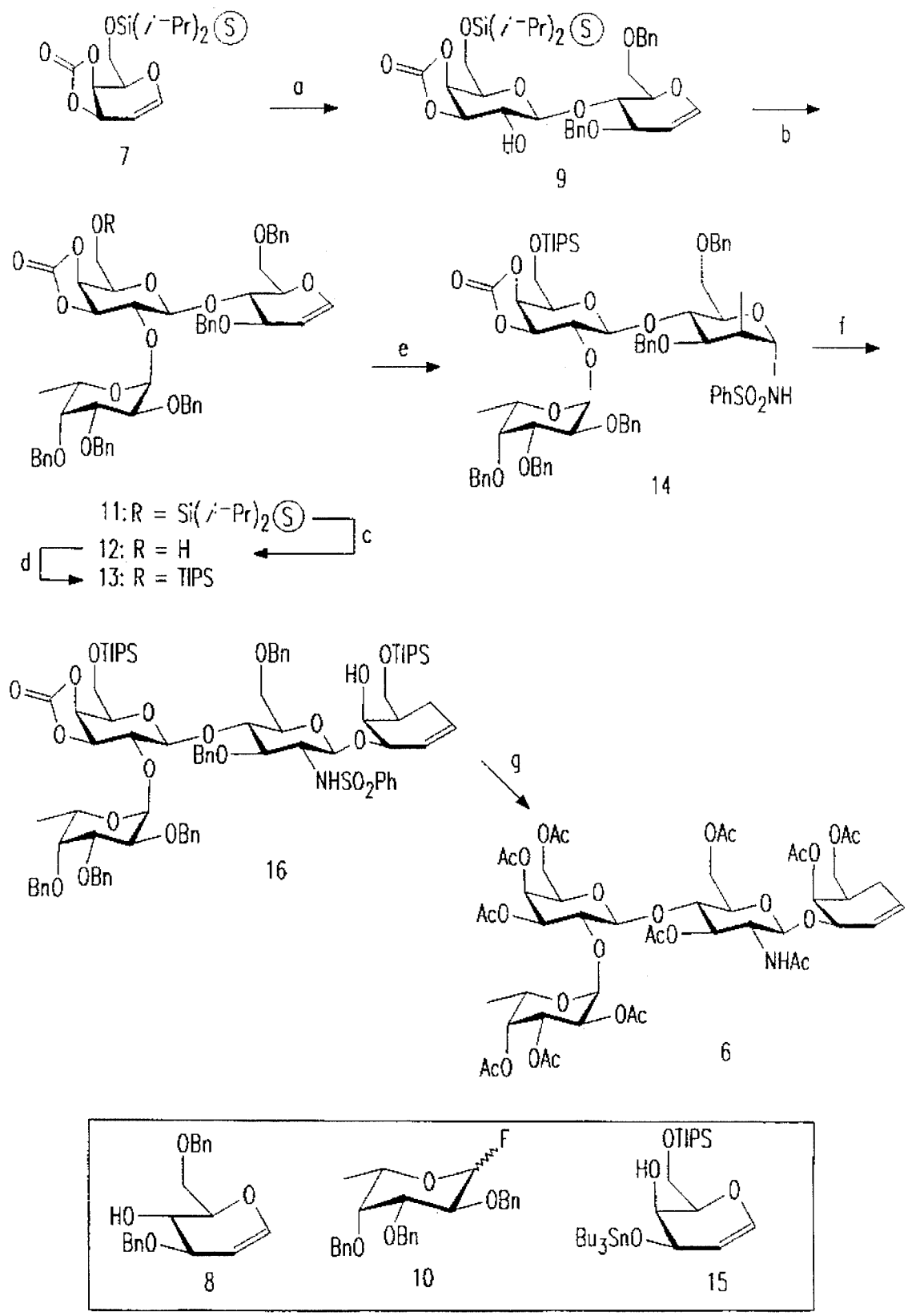
FIG. 6 shows the synthesis of a tetrasaccharide having H-type 2 blood group specificity. Reagents: (a) 1. 3,3-dimethyldioxirane, CH$_2$Cl$_2$; 2. 8, ZnCl$_2$, THF; (b) 10, Sn(OTf)$_2$, di-tert-butylpyridine, THF; (c) TBAF, AcOH, THF; (d) TIPSCl, imidazole, DMF; (e) I (coll)$_2$ClO$_4$, PhSO$_2$NH$_2$, CH$_2$Cl$_2$; (f) 15, AgBF$_4$, 4A M.S., THF; (g) 1. TBAF, AcOH, THF; 2. Na/NH$_3$; 3. Ac$_2$O, pyridine.
Figure 7A:
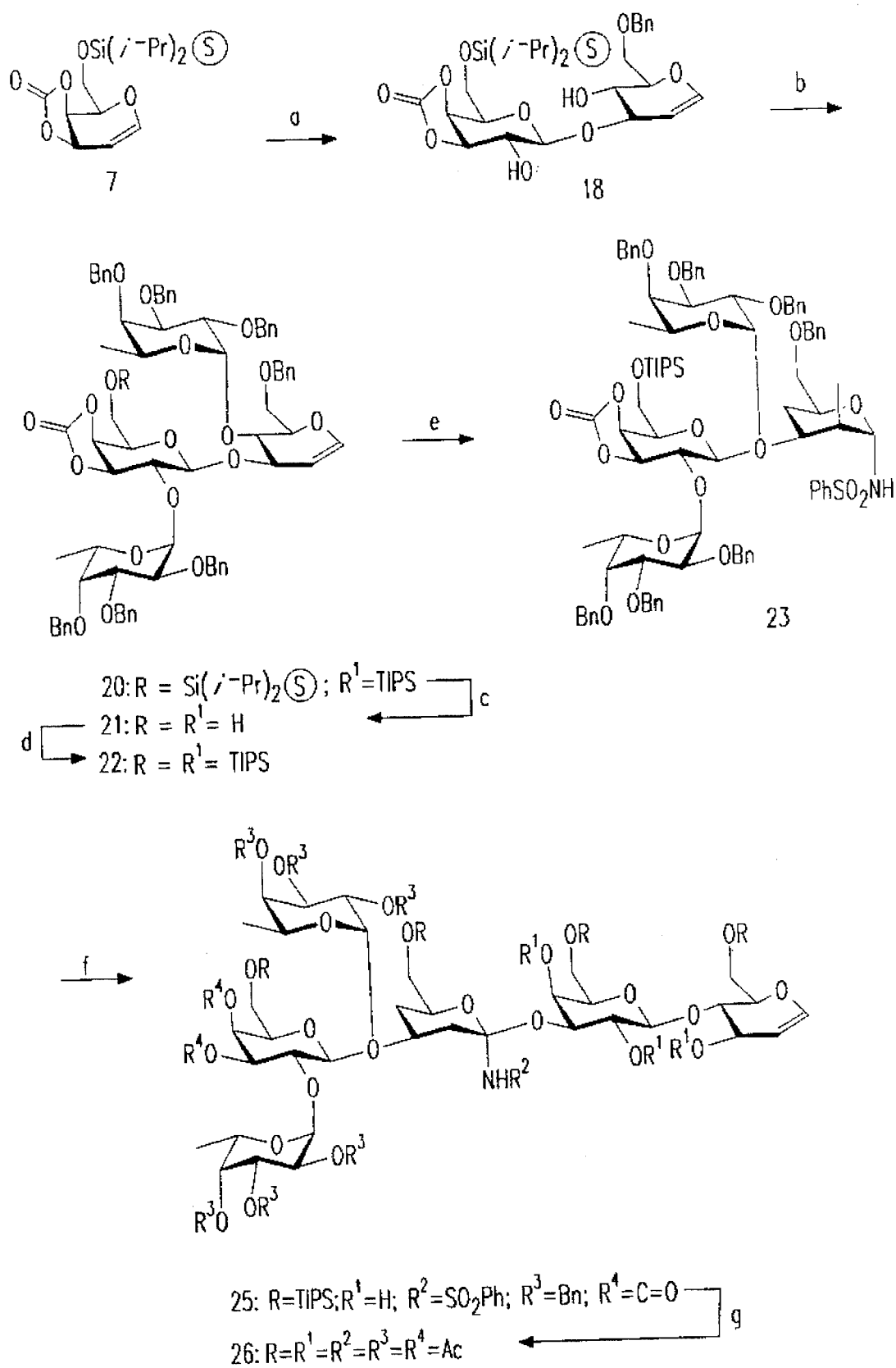
FIGS. 7a and 7b show the synthesis of a Le$^b$ hexasaccharide in bioconjugatable form. Reagents: (a) 1. 3,3-dimethyldioxirane, CH$_2$Cl$_2$; 2. 19, ZnCl$_2$, THF; (b) 10, Sn(OTf)$_2$ di-tert-butylpyridine, THF; (c) TBAF, AcOH, THF; (d) TIPSCl, imidazole, DMF; (e) I (coll)$_2$ClO$_4$, PhSO$_2$NH$_2$, CH$_2$Cl$_2$; (f) 24 AgBF$_4$, 4A M.S., THF; (g) 1. TBAF, AcOH, THF; 2. Na/NH$_3$; 3. Ac$_2$O, pyridine; (h) 1. 3,3-dimethyldioxirane, CH$_2$Cl$_2$; 2. allyl alcohol, ZnCl$_2$; 3. NaOMe, MeOH.
Figure 7B:
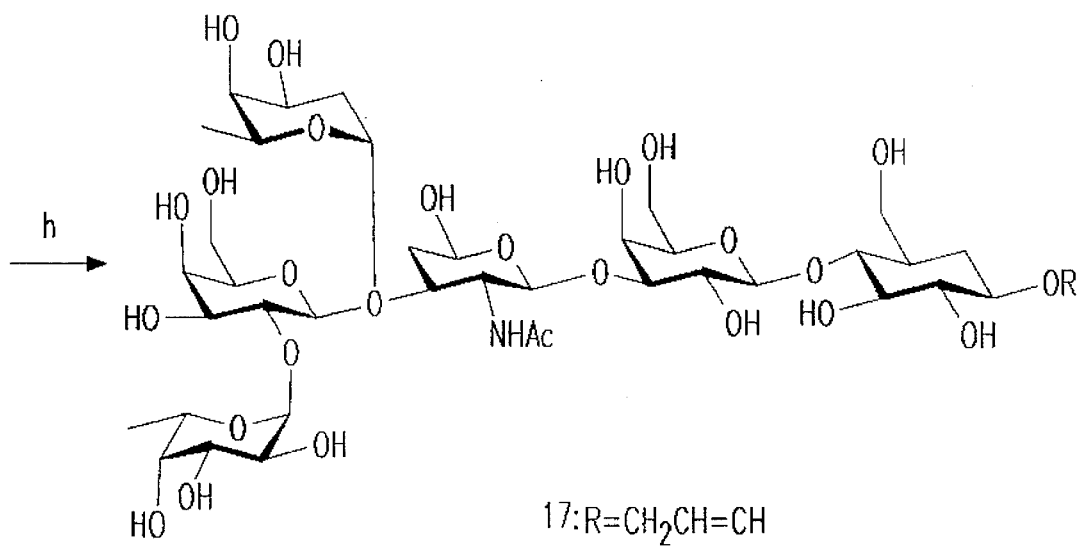
Figure 7B:
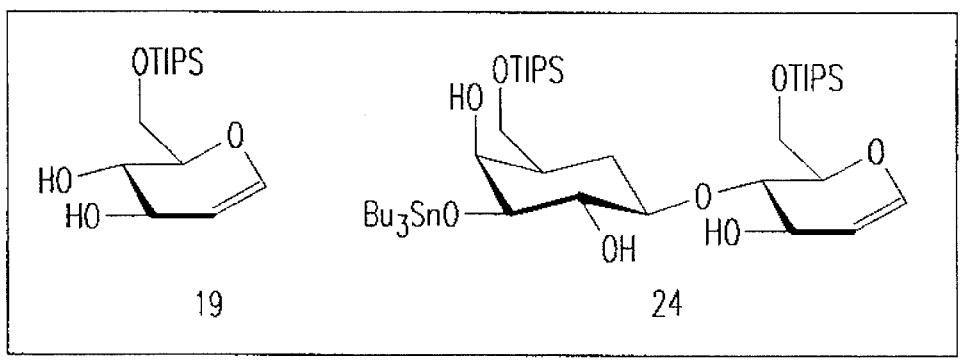
Figure 7B:
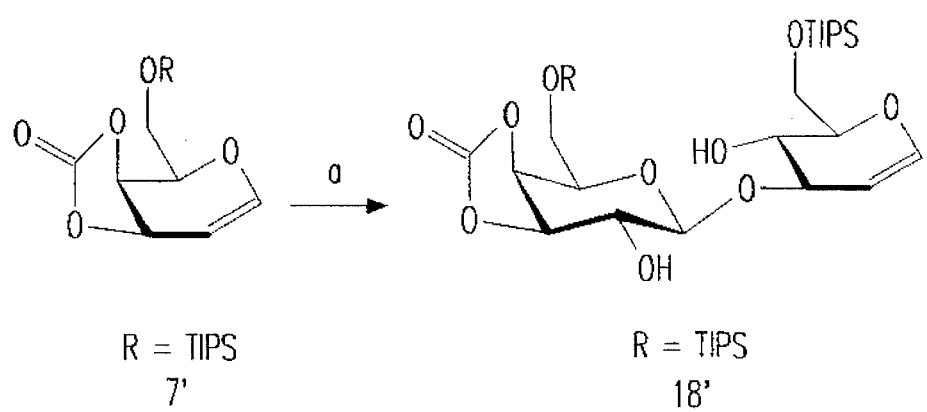

Thus, the synthesis of the full H-type determinant was achieved by sequential polymer- and solution-based maneuvers. The next target was the more complex Le$^b$ hexasaccharide 17. The campaign proceeded as shown in FIG. 6. Polymer-bound galactal 7 was converted to 18 upon epoxidation with 3,3-dimethyldioxirane followed by reaction with glucal derivative 19. This disaccharide diol was then bisfucosylated using fucosyl donor 10 in the presence of $Sn(OTf)_2$ to afford 20. Retrieval from the support with TBAF provided 21, which was obtained in 40% overall yield from 7. Compound 21 reacted with TIPSCl to give 22.

Iodosulfonamide 23, obtained from 22 using $I(coll)_2ClO_4$ and $PhSO_2NH_2$, reacted with lactal derivative 24 in the presence of $AgBF_4$ to provide hexasaccharide glycal 25 in 55% yield. Deprotection of 25 was accomplished in two stages (TBAF to remove the silyl ethers, followed by $Na/NH_3$ reduction to remove the aromatic protecting groups), and the crude product was peracetylated to give 26 in a 51% overall yield. Compound 26 was converted, via the 1,2-anhydrosugar derivative, to allyl glycoside 17, which can be activated by ozonolysis to the aldehyde (R=$CH_2CHO$) for subsequent coupling to a protein by the method of Bernstein and Hall.

In sum, the present invention extends the solid-support glycal assembly method for complex carbohydrate domain synthesis to include the branching patterns critical for biorecognition. Specifically, the determinant for the binding of H. pylori to human gastric epithelium has been stereospecifically fashioned, with simplicity, in a way which provides significant relief from some of the complexities of protecting group manipulations.

Experimental procedure:

6: $^1$H NMR (400 MHz, $CDCl_3$); δ6.39 (d, 1H, J=6.2 Hz, $H_1$ galactal), 5.65 (d, 1H, J=8.9 Hz, NHAc), 5.35 (d, 1H, J=3.8 Hz), 5.33 (m, 1H), 5.29 (d, 1H, J=2.6 Hz), 5.27 (d, 1H, J=3.1 Hz),5.17–5.09 (m, 2H), 4.97–4.90(m,2H), 4.81 (dd, 1H, J=3 Hz, J=6.1 Hz, $H_2$ galactal), 4.75 (d, 1H, J=8.0 Hz), 4.52 (m, 1H), 4.48 (dd, 1H, J=12.0 Hz), 4.44–4.06 (m, 8H), 3.88–3.77 (m, 4H). 3.61 (m, 1H), 2.18–1.97 (m, 33H, $COCH_3$), 1.18 (d, 3H, J=6.5 Hz, $CH_3$ fucose); $^{13}$C NMR ($CDCl_3$): δ170.80, 170.77, 170.72, 170.67, 170.62, 170.34, 170.21, 170.09, 170.01, 169.99, 169.65, 144.92 ($C_1$ galactal), 100.22, 98.83, 98.58, 95.55, 74.48, 73.38, 73.13, 73.06, 71.48, 71.01, 70.68, 67.97, 67.42, 67.18, 67.05, 65.94, 64.83, 62.35, 62.22, 60.88, 60.37, 54.21, 23.23, 22.15, 20.85, 20.82, 20.79, 20.76, 20.65, 20.61, 20.57, 15.51, ($C_6$ fucose); IR (thin film): 3368.7 (NH),2965 6, 2934.6, 1746.5, (C=O), 1537.5, 1435.9, 1371.3, 1228.5, 1065.0, 1046.0;[α]$_D^{23}$=–51.1° (c 1.8, $CH_2Cl_2$); HRMS (FAB); calcd. for $C_{46}H_{632}NNaO_{28}$: m/z=1100.3434, found 1100.3436.

21: Polymer-bound galactal 7 (loading=0.85 mmol glycal/ g), which had been placed in a round-bottom flask equipped with a fritted outlet, was suspended in $CH_2Cl_2$ under $N_2$, cooled to 0° C., and then treated with a solution of 3,3-dimethyldioxirane. The mixture was stirred (teflon-coated magnetic stir bar) for 40 min. at 0° C., after which time solubles were removed by filtration through the fritted outlet ($N_2$ pressure). The polymer bound 1,2 anhydrosugar was evacuated (ca. 0.1 torr) for several hours in order to dry the material for the next step. This material was once again placed under $N_2$ before being treated with 19 (~10 molar equivalents as a 0.5M solution in THF). The suspension was cooled to –40° C., and treated with $ZnCl_2$ (~2 molar equivalents as a 1.0M solution in THF). The reaction mixture was allowed to slowly warm to rt (over ca. 2 h), and then stirred an additional 3–4 h. Solubles were removed by filtration, and polymer 18 was washed several times with THF and then dried in vacuo. To compound 18 was added, in a glove bag, solid Sn(OTf)$_2$ (~molar equivalents), and the mixture was placed under N$_2$ and cooled to 0° C. before being treated with 10 (~5 molar equivalents as a 0.2M solution in THF and di-tert-butylpyridine (~8 molar equivalents). The suspension was allowed to warm to rt and stirred 8–10 h. The mixture was rinsed with anhydrous THF (2 times), 1,4-dioxane (2 times), again with THF, and then dried in vacuo. Compound 20 (100 mg) was suspended in THF, treated with a 1:3 mixture of AcOH and TBAF (~0.2M in TBAF, ~10 molar equivalents), and the mixture was stirred for 18 h at 40° C. The polymer was rinsed with THF (3 times), and the combined rinsings were concentrated and purified by column chromatography on silica gel (1:1 EtOAc: hexanes). Compound 21 (18 mg) was obtained as a colorless solid (40% overall yield from 7): $^1$H NMR (400 MHz, CDCl$_3$): δ7.40–7.25 (m, 30H, Ar H), 6.18 (d, 1H, J=6.0 Hz, H$_1$ glucal), 5.26 (d, 1H, J=3.5 Hz, H$_1$ fucose), 5.09 (d, 1H, J=3.7 Hz, H$_1$ fucose), 4.96 (t, 2H, J=10.8 Hz, PhCH$_2$), (4.90–4.56 (m, 13H), 4.43 (m, 1H), 4.15–4.06 (m, 4H), 3.97 (dt, 1H, J=8.3 Hz, J=2.4 Hz), 3.87–3.65 (m, 10H), 3.64 (d, 1H), 3.57 (d, 1H), 2.69 (br, 1H, OH), 2.52 (br, 1H, OH), 1.11 (d, 3H, J=7.0 Hz, fucose), 1.09 (d, 3H, J=7.0 Hz, CH$_3$ fucose); $^{13}$C NMR (CDCl$_3$): ≠153.37 (C=O), 145.75 (C$_1$ glucal), 138.60, 138.52, 138.19, 137.61, 128.55, 128.52, 128.44, 128.24, 128.16, 128.07, 127.62, 127.56, 127.45, 98.71, 98.38, 97.65, 97.34, 79.26, 78.87, 78.67, 78.01, 77.79, 77.65, 76.37, 76.10, 74.92, 74.40, 74.16, 73.95, 72.86, 72.64, 72.53, 67.43, 67.29, 61.31, 60.90, 16.65 (C$_6$ fucose), 16.53 (C$_6$ fucose); IR (thin film): 3467.0 (OH), 3029.6, 2923.6, 1807.2 (C=O), 1647.3, 1496.0, 1453.5, 1358.1, 1240.2, 1095.6, 1049.2, 738.5, 697.2; [α]$_{D23}$=−82.5° (c 0.4, CH$_2$Cl$_2$); HRMS (FAB); calcd. for C$_{67}$H$_{74}$NaO$_{18}$: m/z=1189.4772, found 1189.4757.

25: To a mixture of 23 (60 mg, 34 μmol) and powdered 4A molecular sieves (200 mg) under N$_2$ was added, via canula, a solution of 24 (0.21 mmol) in anhydrous THF (1.5 mL). The stirred suspension was cooled to −78° C. before being treated with a solution of AgBF$_4$ (0.21 mmol) in 0.25 mL of anhydrous THF. The mixture was stirred and allowed to slowly warm to rt overnight. The suspension, which had developed a bright-yellow color, was heated, with stirring, at 45° C. for an additional 36 h, until the TLC (2.5 EtOAc:hexanes) showed no trace of 23. The mixture was treated with saturated aqueous NH$_4$Cl (5 mL) and then extracted with EtOAc (3×10 mL), and the organics were dried over MgSO$_4$. The crude product was purified by silica gel chromatography (1:3 EtOAc:hexanes) to give 25 as a colorless oil (42 mg, 55%): $^1$H NMR (400 MHz, acetone-d$_6$): δ8.17(d, 2H, J=7.3 Hz, PhSO$_2$), 7.50–7.20 (m, 33H, ArH), 6.52 (d, 1H, J=10.5 Hz, NH), 6.30 (d, 1H, J=6.0 Hz, H$_1$ glucal), 5.35–5.32 (m, 2H), 5.25 (d, 1H, J=7.9 Hz ), 5.15 (m, 2H), 4.99–4.92 (m, 3H), 4.86–4.52 (m, 14H), 4.45 (dd, 1H, J=7.91 Hz, J=2.4 Hz), 4.32–4.23 (m, 3H), 4.22 (dd, 1H), 4.17 (d, 1H, J=10.1 Hz), 4.08–3.84 (m, 18H), 3.79–3.73 (m, 2H), 3.66 (m, 1H), 3.55 (t, 1H, J=6 Hz), 3.50 (dd, 1H, J=9.7 Hz), 1.33 (d, 3H, J=6.5 Hz, CH$_3$ fucose), 1.31 (d, 3H, J=6.4 Hz, CH$_3$ fucose), 1.20–0.98 (m, 84H, 3×Si(i-Pr)$_3$); $^{13}$C NMR (acetone-d$_6$): 145.66 (C=O), 132.72, 131.48, 131.45, 131.28, 131.16, 130.77, 130.48, 121.31, 120.11, 119.86, 119.78, 119.25, 95.63, 94.70, 91.37, 89.64, 89.31, 86.52, 73.38, 72.24, 71.00, 70.71, 70.37, 69.80, 69.59, 69.06, 68.23, 67.92, 67.38, 67.10, 66.49, 65.67, 65.33, 64.60, 64.34, 64.03, 63.45, 63.30, 59.46, 58.83, 58.37, 54.45, 53.32, 49.86, 19.67 (C$_6$ fucose), 18.42 (C$_6$ fucose), 9.55, 9.48, 9.45, 9.31, 9.23, 3.82, 3.70, 3.64; IR (thin film): 3491.9 (OH), 3030.1, 2941.2, 2865.5, 1835.8, 1819.5, 1649.8, 1496.2, 1462.3, 1349.9, 1245.5, 1155.2, 1095.1, 1049.4, 882.2, 734.8, 692.0; [α]$_{D23}$=−33.8° (c 2.0, CH$_2$Cl$_2$); HRMS (FAB): calcd for $^{12}$C$_{120}$$^{13}$CH$_{179}$NNaO$_{29}$SSi$_4$: m/z= 2278.1292, found 2278.1296.

17: $^1$H NMR (400 MHz, CD$_3$OD): δ6.00 (m, 1H, J=5.6 Hz, CH$_2$CH=CH$_2$), 5.37 (dd, 1H, J=1.6 Hz, J=7.3 Hz, CH$_2$CH=CH$_2$), 5.20 (dd, 1H, J=1.6 Hz, J=9.5 Hz, CH$_2$CH=CH$_2$), 5.18 (d, 1H, J=3.9 Hz, H$_1$ fucose), 5.10 (d, 1H, J=3.8 Hz, H$_1$ fucose), 4.64 (d, 1H, J=6.9 Hz), 4.45 (d, 1H, J=7.4 Hz), 4.43–4.23 (m, 2H), 4.27 (dd, 1H, J=9.3 Hz, J=10.6 Hz), 4.23–4.11 (m, 2H), 4.02–3.29 (m, 31H), 2.06 (s, 3H, NAc), 1.31 (d, 3H, J=6.6 Hz, CH$_3$ fucose, 1.29 (d, 3H, J=6.6 Hz, CH$_3$ fucose); $^{13}$C NMR (CD$_3$OD): δ173.20 (C=O), 135.73 (CH$_2$CH=CH$_2$), 105.13, 103.30, 102.49, 101.62, 99.63, 96.86, 80.79, 80.67, 78.44, 76.49, 75.89, 74.80, 74.59, 73.94, 73.61, 73.40, 71.55, 71.38, 71.16, 70.42, 70.26, 70.14, 67.77, 67.30, 67.21, 62.79, 62.34, 61.99, 55.54, 22.97 (NAc), 16.65 (2 C's, C$_6$ fucose); IR (thin film): 3376.6 (OH), 2924.2, 1652.5 (C=O), 1383.1, 1032.4; [α]$_{D23}$=12.8° (c 0.25, MeOH); HRMS (FAB): calcd. for C$_{41}$H$_{69}$NaO$_{29}$: m/z=1062.3853, found 1062.3837

What is claimed is:

1. A compound having the structure:

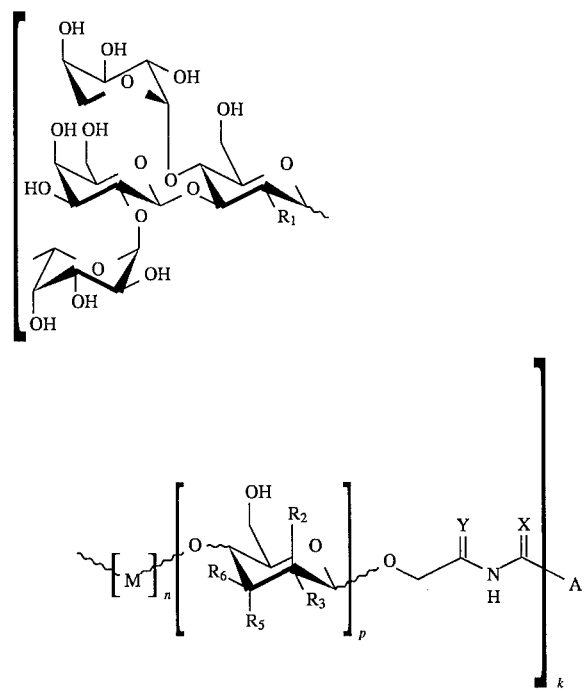

wherein A is selected from the group consisting of (i) an amino acid bearing an ω-amino group or an ω-(C=O)— group, (ii) an amino acid residue of a peptide, which residue bears an ω-amino group or an ω-(C=O)— group, and (iii) an amino acid residue of a protein, which residue bears an ω-amino group or an ω-(C=O)— group;

wherein R$_1$ is H, OH, NH$_2$ or NHR$_4$, where R$_4$ is SO$_2$Ph, a linear or branched chain alkyl or acyl group, or an aryl group;

wherein M has the structure:

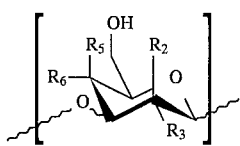

wherein n is an integer from 0 to 18, and where n is greater than 1, each M is independently the same or different;

wherein p is either 0 or 1;

wherein $R_2$, $R_3$, $R_5$ and $R_6$ are independently the same or different and are H or OH, with the proviso that $R_2$ and $R_3$ are not both OH, and $R_5$ and $R_6$ are not both OH;

wherein each wavy line between a carbon atom and an oxygen atom denotes an R or S configuration at the carbon atom;

wherein X and Y are independently the same or different and are $H_2$ or O; and wherein k is an integer greater than or equal to 1, with the proviso that when A is an amino acid bearing an ω-amino group or an ω-(C=O)— group, k is equal to 1.

2. The compound of claim 1, wherein A is lysine or a lysine residue.

3. The compound of claim 1, wherein A is glutamic acid or a glutamic acid residue.

4. The compound of claim 1, wherein A is aspartic acid or an aspartic acid residue.

5. The compound of claim 1, wherein A is an amino acid residue of a globular protein.

6. The compound of claim 5, wherein the globular protein is selected from the group consisting of bovine serum albumin and human serum albumin.

7. The compound of claim 1, wherein k is 1.

8. The compound of claim 1, wherein n and p are both equal to 0.

* * * * *